(12) United States Patent
Stephan

(10) Patent No.: US 8,641,686 B2
(45) Date of Patent: Feb. 4, 2014

(54) ANTI-BIOFILM INTRAVASCULAR CATHETER

(76) Inventor: Rabie Stephan, Amherst, NY (US)

( * ) Notice: Subject to any disclaimer, the term of this patent is extended or adjusted under 35 U.S.C. 154(b) by 0 days.

(21) Appl. No.: 13/354,514

(22) Filed: Jan. 20, 2012

(65) Prior Publication Data
US 2013/0190699 A1 Jul. 25, 2013

(51) Int. Cl.
*A61M 25/00* (2006.01)
*C23C 14/54* (2006.01)
*A61L 24/00* (2006.01)

(52) U.S. Cl.
USPC ............................... 604/264; 427/9; 523/113

(58) Field of Classification Search
USPC ............. 604/264; 428/156–157, 161; 134/42; 427/9; 523/113
See application file for complete search history.

(56) References Cited

U.S. PATENT DOCUMENTS

| | | | |
|---|---|---|---|
| 7,393,501 B2 | 7/2008 | Zumeris et al. | |
| 7,820,284 B2 | 10/2010 | Terry | |
| 7,947,301 B2 | 5/2011 | Bischoff et al. | |
| 2007/0227428 A1* | 10/2007 | Brennan et al. | 114/67 R |
| 2011/0098323 A1 | 4/2011 | Opperman et al. | |
| 2013/0059113 A1* | 3/2013 | Hatton et al. | 428/116 |

OTHER PUBLICATIONS

MG Bourassa et al., Scanning electron microscopy of surface irregularities and thrombogenesis of polyurethane and polyethylene coronary catheters, Circulation 1976;53;992-996, Print ISSN: 0009-7322 Online ISSN: 1524-4539, 1976, American Heart Association, 7272 Greenville Avenue, Dallas, TX 72514.
Ligia R. Rodrigues, Inhibition of Bacterial Adhesion on Medical Devices, Advances in Experimental Medicine and Biology, 1, vol. 715, Bacterial Adhesion, pp. 351-367, 2011.
Sales Brochure of NewView 5000, Publication No. SB-0323 4/01 2M, ZYGO CORPORATION, Laurel Brook Road, Middlefield, CT 06455, USA.
ASME B46.1-2009 Surface Texture, Surface Roughness, Waviness and Lay.
ASME B46 Committee—Surface Texture—Panel Discussion, http://cstools.asme.org/csconnect/pdf/CommitteeFiles/21763.pdf.
ASME B46 Committee—Surface Texture—Panel Discussion, http://cstools.asme.org/csconnect/pdf/CommitteeFiles/21763.pdf, pp. 3 and 4.
Alexander H. Slocum, Precision Machine Design, pp. 81 and 82, ISBN: 9780136909187.

* cited by examiner

*Primary Examiner* — Quynh-Nhu H Vu
(74) *Attorney, Agent, or Firm* — Tracy Jong Law Firm; Tracy P. Jong; Cheng Ning Jong

(57) ABSTRACT

An anti-biofilm catheter comprising a tubing configured to be disposed within a luminal system, wherein the tubing comes in contacting engagement with a blood flow within the luminal system in vivo. The catheter comprises a surface disposed over at least a portion of the tubing, wherein the surface comprises a surface profile having a skewness value of from about −0.01 to about −0.6 such that few or no components of the blood flow is capable of attaching themselves to the surface to encourage biofilm formation. The surface profile further comprises a kurtosis value of from about 2.7 to 3.3.

10 Claims, 41 Drawing Sheets

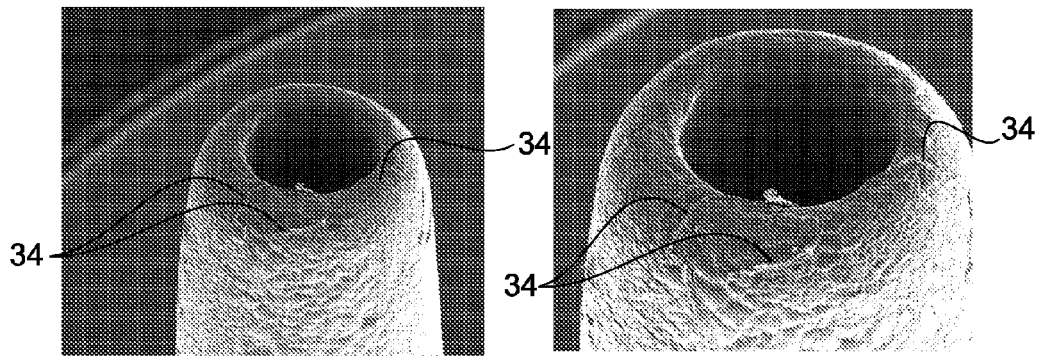
PRIOR ART
FIG. 4E
PRIOR ART
FIG. 4F
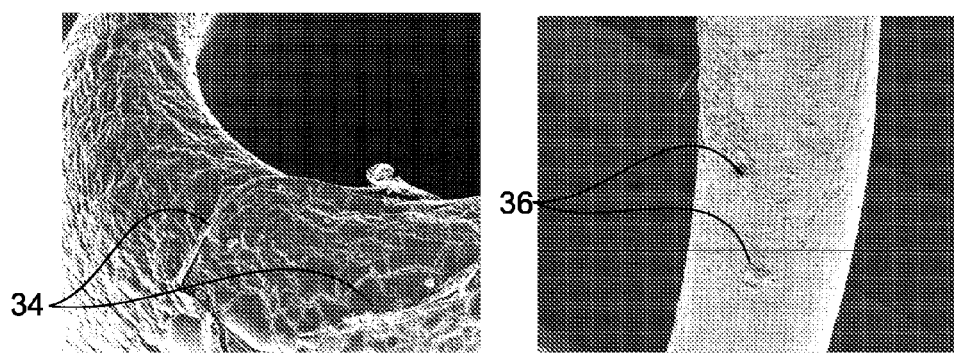
PRIOR ART
FIG. 4G
PRIOR ART
FIG. 4H

Roughness Profile Parameters

| Sample | No. | Ra (µm) | Std Dev | Rz (µm) | Std Dev | Rt (µm) | Std Dev | Sm (µm) | Std Dev |
|---|---|---|---|---|---|---|---|---|---|
| Dry V Tube | 15 | 0.173 | 0.011 | 0.977 | 0.063 | 1.303 | 0.133 | 30.135 | 7.364 |
| Wet Tube 1 | 15 | 0.694 | 0.058 | 4.141 | 0.301 | 5.669 | 0.623 | 28.495 | 2.726 |
| Wet Tube 3 | 15 | 0.397 | 0.046 | 2.710 | 0.506 | 4.017 | 1.046 | 27.905 | 3.239 |

| Sample | Ra (µm) | Rq (µm) | Rsk | Rku | Rz (µm) | Rpk (µm) | Rk (µm) | Rvk (µm) | V1 (µm³) | V2 (µm³) |
|---|---|---|---|---|---|---|---|---|---|---|
| Dry Sample 5 | 0.149 | 0.188 | 0.476 | 3.468 | 1.486 | 0.234 | 0.464 | 0.132 | 194.21 | 77.32 |
| Dry Sample 5 | 0.164 | 0.206 | 0.281 | 3.112 | 1.518 | 0.219 | 0.521 | 0.161 | 177.35 | 98.22 |
| Dry Sample 5 | 0.127 | 0.164 | 0.629 | 3.974 | 1.486 | 0.224 | 0.381 | 0.121 | 207.73 | 66.95 |
| Wet Sample 1 | 0.790 | 0.995 | -0.047 | 3.254 | 5.844 | 0.992 | 2.519 | 1.049 | 586.0 | 727.9 |
| Wet Sample 1 | 0.637 | 0.806 | -0.539 | 3.278 | 4.721 | 0.480 | 2.013 | 1.104 | 239.5 | 895.8 |
| Wet Sample 1 | 0.749 | 0.929 | -0.239 | 2.778 | 4.729 | 0.658 | 2.441 | 0.974 | 359.9 | 727.0 |
| Wet Sample 3 | 0.383 | 0.508 | 1.241 | 5.359 | 3.389 | 0.864 | 1.026 | 0.322 | 1050.6 | 111.1 |
| Wet Sample 3 | 0.415 | 0.665 | 2.856 | 15.017 | 4.372 | 1.490 | 0.928 | 0.374 | 1653.7 | 221.6 |
| Wet Sample 3 | 0.373 | 0.624 | 3.138 | 15.994 | 5.085 | 1.453 | 0.802 | 0.285 | 1633.0 | 169.7 |

*FIG. 14*

ANTI-BIOFILM INTRAVASCULAR CATHETER

BACKGROUND OF THE INVENTION

1. The Field of the Invention

The present invention is directed generally to a surface construction applicable to a temporary implantation of medical devices in vivo and more particularly to an intravascular catheter having surface qualities capable of preventing the formation of biofilm.

2. Background Art

Many solutions have been attempted in combating infections caused by intravascularly implanted medical devices or catheters. The treatment of entry sites of percutaneously implanted devices have dramatically reduced infections caused by the transfer of microbes from the surface tissue or skin of a person or animal to the intravascular, organ or body tissue infections. However, infections due to microbes already present within the body remain serious cause of infections and ill health. Common solutions include but not limited to coating of surfaces with anti-microbial drugs, modification of surface charges, implementation of ultrasonic vibrating devices, etc. However, such solutions may cause negative side effects such as in the case of anti-microbial drugs. Modification of surface charges and implementation of ultrasonic vibrating devices require complicated equipment which not only increase costs but also require constant or periodic power use, sophisticated control and actuating devices.

U.S. Pat. No. 7,947,301 to Bischoff et al. discloses anti-infective articles capable of preventing infection associated with implantation of medical devices include low levels of anti-infective agents, may cover only a fraction of the portion of the medical device and be effective, or may rapidly elute anti-infective agent, without sustained elution. This patent further discloses the use of minocycline and rifampin which can cause negative effects. Minocycline has been known to cause upset stomach, diarrhea, dizziness, unsteadiness, drowsiness, mouth sores, headache and vomiting. Rifampin on the other hand has been known to cause diarrhea, dizziness, drowsiness, gas, headache, heartburn, menstrual changes, mild upset stomach and cramps. As the anti-infection effectiveness of the articles depend on the elution of a drug, various factors such as the size, shape, surface exposure area of the drug used and the environment in the which the articles are disposed and the like can affect the elution rate of the drug. Therefore the elution rate and hence the period of which a drug remains effective can hardly be ascertained.

U.S. Pat. Pub. No. 2011/0098323 discloses an organic compound for combating Gram-positive biofilm-forming bacteria. Timed release of such compound is also problematic as it also depends on its in-situ elution which may not be accurately controlled. In addition, the formulation of such compound involves numerous active compounds which translate to higher materials and manufacturing costs.

U.S. Pat. No. 7,820,284 to Terry discloses microbe-resistant medical devices and methods of making these medical devices. A base coat is applied to at least a portion of a surface of a device. The base coat includes one or more types of antimicrobial particles that are held in the base coat. A polymeric over coat is applied over at least a portion of the base coat. The over coat may be an organic soluble polymer, a water soluble polymer, a hydrogel or any other polymer capable of being coated onto a medical device. The polymer of the over coat is dissolvable in a solvent that does not dissolve the polymeric base coat during application of the over coat. The over coat remains free of the antimicrobial particles by not dissolving the base coat during the over coating process. This patent teaches a process for applying a multi-layer lubricious coating including antimicrobial particles to surfaces of a medical device.

U.S. Pat. No. 7,393,501 to Zumeris et al. discloses an apparatus, system and method for preventing or treating biofilm associated with catheters. A piezo-ceramic element is attached to a catheter, and a vibration processor is connected to the piezo-ceramic element. The vibration processor provides electric signals that generate acoustic vibrations in the piezo-ceramic element, causing vibrations in or around the catheter. These vibrations are administered to disperse microbe colonies, thereby preventing or inhibiting formation of biofilm that may lead to infections. Vibrations may be amplified significantly due to resonance conditions in the catheter balloon, which may be powerful enough to be used to disperse microbe colonies that have grouped around the catheter or are attempting to do so. This patent teaches a positively and in-situ powered device which requires external power and its active administration to prevent further infection.

An article entitling "Scanning Electron Microscopy of Surface Irregularities and Thrombogenesis of Polyurethane and Polyethylene Coronary Catheters" by Bourassa et al. (hereinafter Bourassa) of Vol. 53, No. 6, June 1976 of the Journal of the American Heart Association disclosed adherent thrombi on all external surfaces of Ducor polyurerathane and polyetylene catheters. Bourassa went on to summarize their finding as:

"Following routine coronary artriography, surface irregularities and thrombogenesis of the inner and outer wall of six Ducor polyurethane and six RPX polyethylene coronary catheters were studied by scanning electron microscopy. Polyurethane catheters had rough and highly irregular external and internal surfaces. All catheters showed adherent thrombi on their external surface. The internal surface of three catheters showed evidence of thrombosis. Polyethylene differed from polyurethane in several respects. Although the external surface had an irregular and wavelike appearance, the internal surface was smooth and regular. Two polyethylene catheters showed thrombi on their external surface. The internal surface of one catheter showed single platelets in one area. These results confirm recent reports showing that internal and external surface irregularities play a major role in the initiation of thrombosis in and on intravascular catheters. They stress the need for high quality catheter materials with smooth and regular surface in the prevention of thromboembolic complications from coronary arteriography."

It is evident from the foregoing statement that a smooth and regular surface is thought to be of superior quality in preventing thromboembolic complications. As will be disclose hereinafter, such hypothesis may be problematic and the contrary may be true.

A biofilm is a community of sessile, stably attached microorganisms, especially bacteria, embedded in a hydrated matrix of extracellular polymeric substances exhibiting growth properties that are distinguished from those of planktonic, free-living microorganisms. Biofilms represent a target of new compositions for inhibiting, reducing, preventing, and removing microbial infections, and are believed to be partly responsible for increasing the rates of antibiotic resistance. It is thought that upwards of 60% of all nosocomial (hospital-derived) infections are due to biofilms, whose role in contaminating medical implants is now well established. Central venous catheters (CVCs) pose the greatest risk of device-related infections with infection rates of 3 to 5% and account for the most serious and costly healthcare-associated infections (See for example, Donlan and Costerton, Clin. Microbiol. Rev., Vol. 15, No. 2, pp. 167-193, 2002; Davey and O'Toole, Microbiol. Mol. Biol. Rev., Vol. 64, No. 4, pp. 847-867, 2000).

One approach to managing biofilm infections is to identify the microorganism(s) in the biofilm and to find antibiotic or biocidal agents capable of killing the microorganisms. A major limitation of this approach is that models for testing the efficacy of these agents to not sufficiently represent a biofilm environment. Biofilm bacteria can be up to 1.000-fold more resistant to antibiotic treatment than the same organism grown planktonically.

Biofilm bacteria are also more resistant to biocides, such as peroxide, bleach, acids, and other biocidal agents.

In spite of the dramatic differences in susceptibility to antimicrobial agents between planktonic and sessile, biofilm microorganisms, current approaches for targeting biofilm microorganisms are insufficient in addressing this discrepancy. Antimicrobial efficacy testing often employs standard broth microdilution methods reflecting antibiotic efficacy in planktonic, rather than biofilm systems. Accordingly, broad numbers of prospective antibiotic- and biocidal agents have been identified without any expectation of success in the more "real" biofilm world.

The mechanisms by which resistance to antibiotic or biocidal agents is achieved remain subject to speculation. In recent years, biofilm-based infections attributed to medical devices, such as catheters, prosthetic heart valves, contact lenses, and intrauterine devices have received increased attention. Despite circumstantial evidence suggesting biofilm to be a major culprit responsible for chronic wounds, their role in chronic wounds remains poorly understood.

Thus, there arises a need for a catheter which does not rely on the presence and release of antibiotics, biocidal agents or other medicines for combating biofilm formation as the medicine may create negative effects. An antimicrobial-coated catheter relies on the presence of an antimicrobial substance and its regulated release to be effective. As the elution rate of such substance can vary from person to person, close monitoring of the effectiveness of such substance is still required. Further, there arises a need for a catheter that is reliable and effective in combating biofilm formation in all conditions and a catheter which does not require close monitoring and external power to prevent microbe growth.

SUMMARY OF THE INVENTION

The present invention is directed toward an anti-biofilm surface comprising a surface profile having a skewness value of from about −0.01 to about −0.6. The surface profile further comprises a kurtosis value of from about 2.7 to about 3.3. The surface comprises a material selected from a group consisting of polyurethane, polyethylene and healthcare silicone.

In a more specific embodiment, the present invention is directed toward an anti-biofilm catheter comprising a tubing configured to be disposed within a luminal system, wherein the tubing comes in contacting engagement with a blood flow within the luminal system. The catheter comprises a surface disposed over at least a portion of the tubing, wherein the surface comprises a surface profile having a skewness value of from about −0.01 to about −0.6 such that few or no components of the blood flow is capable of attaching themselves to the surface to encourage biofilm formation. The surface profile further comprises a kurtosis value of from about 2.7 to about 3.3.

Accordingly, it is a primary object of the present invention to provide an anti-biofilm catheter which requires no external power and where the catheter has surfaces not configured for timed release of drugs to combat biofilm colonization on the surfaces.

It is another object of the present invention to provide an anti-biofilm catheter that is simple to use and does not require the user of such catheter to follow special instructions for monitoring and effective use of the catheter.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 4E is an SEM image of a used prior art catheter at 74× magnification depicting fiber strands that developed in a tip.

FIG. 4F is an SEM image of a used prior art catheter at 121× magnification depicting fiber strands that developed in the tip of FIG. 4E.

FIG. 4G is an SEM image of a used prior art catheter at 245× magnification depicting fiber strands that developed in the tip of FIG. 4E.

FIG. 4H is an SEM image of a used prior art catheter at 37× magnification depicting surface irregularities.

FIG. 9I is an SEM image of the post wet test uncoated polyurethane tubing at 1020× magnification depicting a close-up view of collection of red blood cells on its surface.

FIG. 9J is an SEM image of the post wet test uncoated polyurethane tubing at 5040× magnification depicting a close-up view of collection of red blood cells on its surface.

FIG. 14 is a table of area statistics of dry sample 5, wet samples 1 and 3.

PARTS LIST

Figure 1:
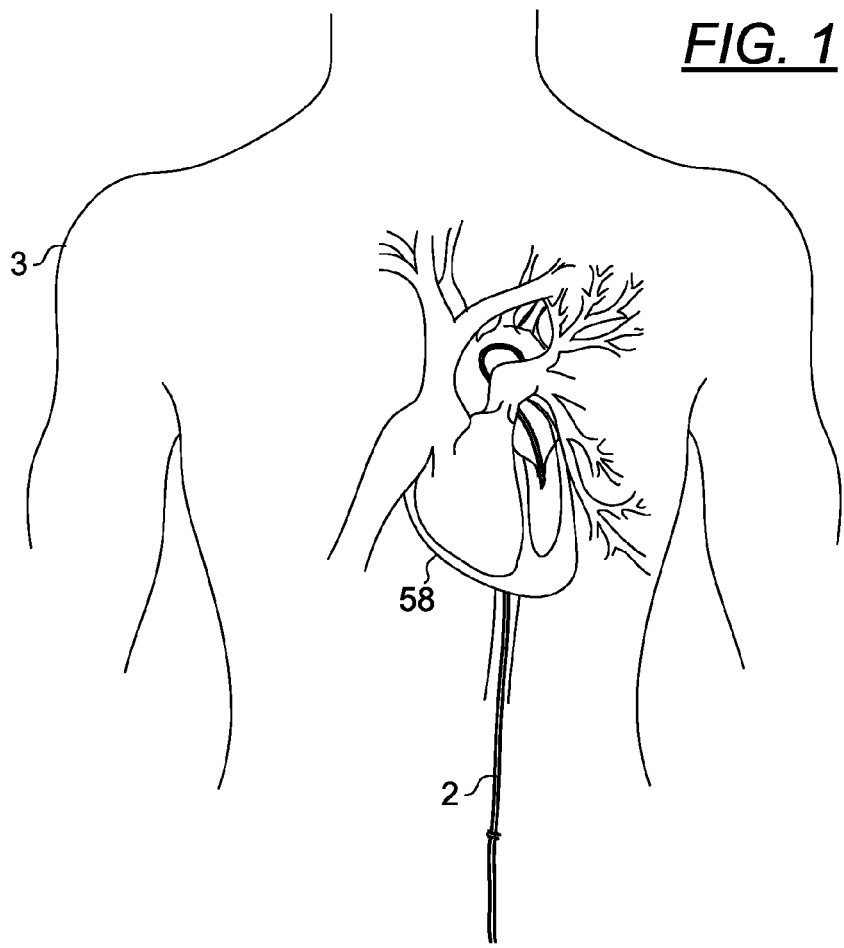
FIG. 1 is a diagram depicting an environment in which a catheter is used.

2—catheter
3—patient
4—tubing
6—tip of tubing
8—interface of tip of tubing and tubing
10—ridges
12—raised surface feature
14—length of raised surface feature
16—width of raised surface feature
18—cutout
20—voids, bumps, striations
22—larger and more thinly spread surface feature
24—mottle
26—liner like ridge
28—length of liner like ridge
30—width of liner like ridge
32—deep abrasion
34—fiber strand
36—surface irregularities
38—length of surface irregularities
40—crack
42—fine crazing
44—fine open structures
46—length of raised surface feature of sample 5
48—width of raised surface feature of sample 5
50—length of raised surface feature of sample 5
52—width of raised surface feature of sample 5
54—length of raised surface feature of sample 5
56—width of raised surface feature of sample 5

58—heart
60—cut tip of tubing
62—lumen of catheter
64—side port aperture
66—external surface of catheter
68—internal surface of catheter
70—proud particles
72—red blood cells
74—surface plot
76—irregular shaped features
78—step of collecting surface profile parameter values
80—step of comparing collected surface profile parameter values to their corresponding predetermined acceptable ranges which correspond to a surface suitable to be used as an anti-biofilm surface
82—step of treating catheter surface for altering its surface profile structure

PARTICULAR ADVANTAGES OF THE INVENTION

The present invention does not require temporary modification of the surface properties of a catheter to provide its anti-adhesive property and antimicrobial activity. The effectiveness of anti-biofilm strategies based on the modification of the chemical properties of the substrate have been found to be limited and varies greatly depending on bacterial species, mainly due to the diverse environments into which a catheter is placed and the multiplicity of ways in which organisms can colonize surfaces.

DEFINITION OF SURFACE PROFILE AND RELATED TERMS

Ra—the arithmetic average height. In practice, "Ra" is the most commonly used roughness parameter. Mathematically, Ra is computed as the average distance between each roughness profile point and the meanline.

Rq—Root Mean Square (RMS) Amplitude

The root mean squared amplitude. This is a very common method for describing variation in mathematics, electronics, statistics, etc., as it represents the "standard deviation" (sigma).

Rt—Total Peak-to-Valley height (over the entire assessment length). The distance between the highest peak and deepest valley is reported as a positive value regardless of the location of the peak and valley within the assessment length.

Rz—the average peak to valley roughness based on one peak and one valley per sampling length. The Rz value is based on the determination of the peak to valley distance in each sampling length. These individual peak to valley distances are averaged, resulting in the Rz value.

Rsk—a profile's skewness. This describes the shape of the distribution of profile points. Positive skewness values indicate a profile with dominant, isolated peaks, while negative values indicate dominant, isolated valleys.

Rku—a profile's kurtosis. This describes the shape of the distribution of profile points. A Gaussian normal distribution results in a kurtosis of 3.0. Kurtosis values greater than 3.0 indicate a profile with extreme peaks and/or valleys (outside the normal statistical limits of a Gaussian distribution). Kurtosis values less than 3.0 indicate a profile without extreme peaks and/or valleys.

The Rk family of parameters
Rk—Core (Kernel) Roughness
Rpk—Reduced Peak Height
Rvk—Reduced Valley Depth The Rk family of parameters describe regions of the bearing ratio curve. The basis of the parameters is the establishment of the core (kernel) of the profile. This is based on the determination of the more horizontal region of the bearing ratio curve through the use of a 40% window. The extension of the line through the 40% window establishes the core roughness of the profile. The regions above and below the core are considered to be peaks and valleys (respectively).

Sm—Mean spacing of profile irregularities.

The term "used" as used herein throughout is used to reference a catheter or sample surface which has been wet tested or disposed in a blood flow of normal blood flow condition or in vivo luminal system. A wet test as used herein can also be carried out by immersing a catheter or sample in a static blood bath in a controlled environment (e.g. an incubator) of 37 degrees Celsius for thirty six hours. This is followed by rinsing the catheter or sample in a stream of saline, without exposing it to any types of abrasive contact with a solid surface such as a brush, towel, etc.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

DETAILED DESCRIPTION

Figure 2A:
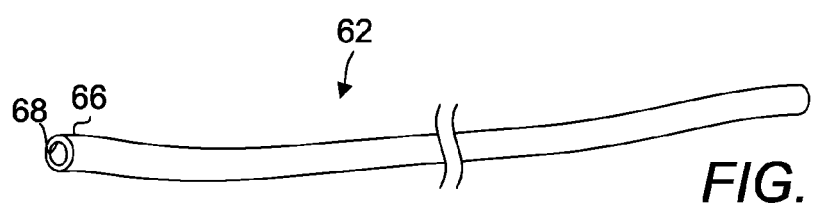
FIG. 2A is a close-up perspective view of an unaltered catheter.

FIG. 1 is a diagram depicting an environment in which a catheter 2 is used. FIG. 2A is a close-up perspective view of an unaltered catheter 2. In this example, a left heart catheterization is shown where a catheter is inserted via the aorta into the left side of the heart 58 to obtain diagnostic information about the left side of the heart or to provide therapeutic interventions in certain types of heart conditions. While in use, the external surface 66 of catheter comes in direct contact with blood flow of a luminal system of the patient 3 while the internal surface 68 of catheter may become engaged with a guide wire, medical solution and the like. Exposure of the external and internal surfaces 66, 68 to biological or non-biological materials increase the opportunities for adhesion of such materials to these surfaces which then provide substrate for adhesion and growth of biofilm which can cause infections.

The term "biofilm" denotes an extracellular matrix in which microorganisms are dispersed and/or form colonies. The biofilm typically is made of polysaccharides and other macromolecules. In addition, in the present invention, the phrase "inhibiting a biofilm," and like phrases, means the prevention of biofilm growth, reduction in the rate of biofilm growth, partial eradication of existing biofilm, and/or complete eradication of existing biofilm. According to an article entitling "Bacterial biofilms: a common cause of persistent Infections" of Science Magazine (Vol. 284, Pages 1318-1322 of Costerton et al., May 21, 1999), more than half of the infectious diseases that affect mildly immune-compromised individuals involve bacterial species that are commensal in humans or are common in our environment. For a successful implant, tissue integration occurs prior to appreciable bacterial adhesion, thereby preventing colonization at the implant. However, host defenses often cannot prevent further colonization if bacterial adhesion occurs before tissue integration. Therefore, it is imperative to provide a catheter having surfaces which prevent collection of adherents that can encourage biofilm growth.

Figure 2B:
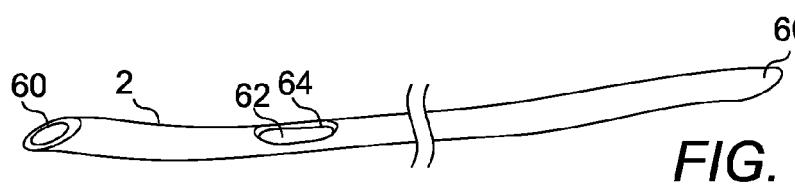
FIG. 2B is a close-up perspective view of an altered catheter.

FIG. 2B is a close-up perspective view of an altered catheter 2. It has long been known to taper the tip 60 of a catheter 2, in particular, a peripherally inserted intravenous catheter in order to ease the insertion process. It has further been found that many products today have a dual bevel formed at the catheter tip 60 (see FIG. 3A). In some circumstances, a tapered tip is cut to length in-situ with unsanitary cutting devices. Such practice results in cut surfaces having different properties than those of factory formed catheter tips and should be avoided as the cut surfaces may have surface profiles suitable for biofilm growth.

In one embodiment according to the present invention, fabricating the catheter to appropriate lengths, e.g., 18, 24, 30, 36 inches, renders the practice of cutting to form tapered tips unnecessary. The present catheter therefore retains consistent surface properties intended throughout its entire length.

Another feature which may also be found in a catheter includes a side port aperture 64 that is open to a lumen 62 of a catheter. The side port aperture 64 is configured for receiving another device for use in conjunction with the catheter.

In Applicant's search for a suitable biofilm surface, the Applicant analyzed three different surfaces, i.e., the first, second and third surfaces. Two samples are tested for the first surface, i.e., samples 1 and 2. Two samples are tested for the second material, i.e., samples 3 and 4. Sample 5 represents the third surface. The third surface includes an uncoated polyurethane tubing.

Figure 3A:
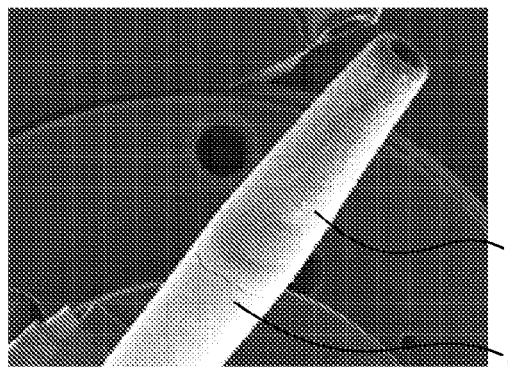
FIG. 3A is a Scanning Electron Microscopy (SEM) image of a tip of a prior art catheter at 20× magnification.
Figure 3B:
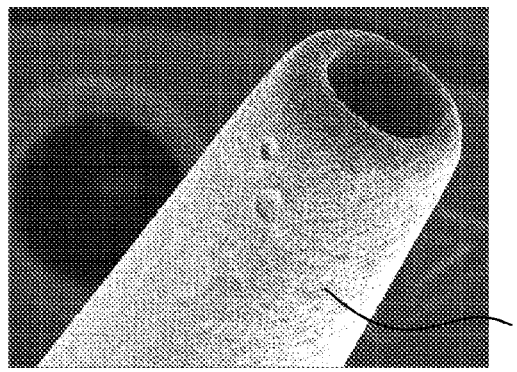
FIG. 3B is an SEM image of a tip of a prior art catheter at 64× magnification depicting multiple surface roughness morphologies.
Figure 3C:
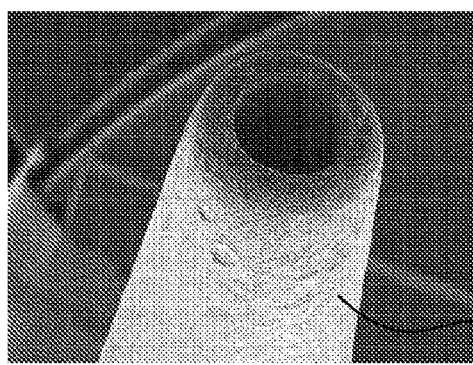
FIG. 3C is an SEM image of a tip of a prior art catheter at 62× magnification depicting multiple surface roughness morphologies.
Figure 3D:
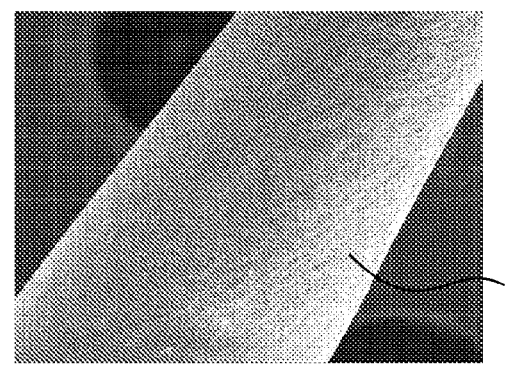
FIG. 3D is an SEM image of a tip of a prior art catheter at 63× magnification depicting multiple surface roughness morphologies and the general conical shape of the tip.
Figure 3E:
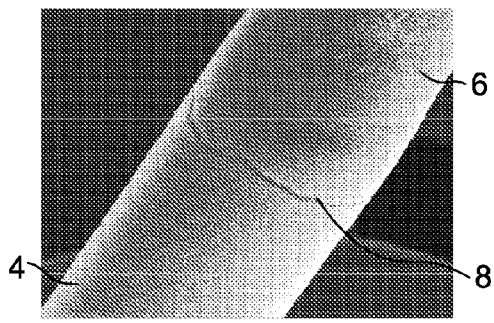
FIG. 3E is an SEM image of a tip of a prior art catheter at 46× magnification depicting multiple surface roughness morphologies and the interface between the tip of a tubing and the tubing.
Figure 3F:
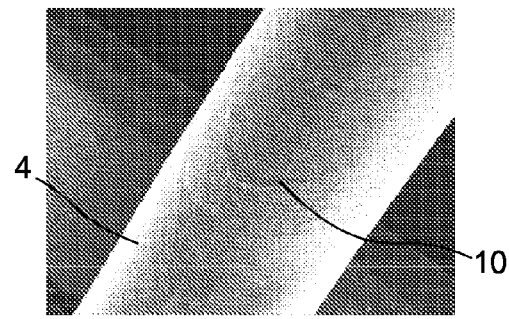
FIG. 3F is an SEM image of a prior art catheter at 47× magnification depicting surface ridges on a tubing.
Figure 3G:
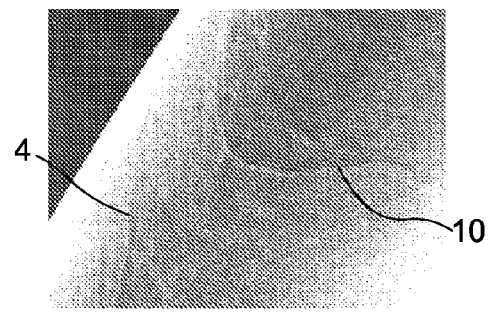
FIG. 3G is an SEM image of a prior art catheter at 89× magnification depicting the surface ridges of FIG. 3F.
Figure 3H:
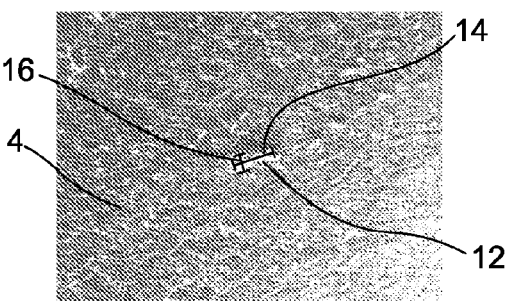
FIG. 3H is an SEM image of a prior art catheter at 390× magnification depicting the raised surface feature of a catheter.
Figure 3I:
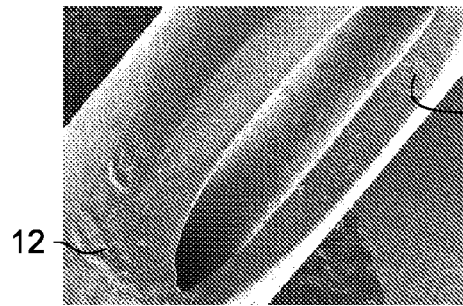
FIG. 3I is an SEM image of a prior art catheter at 59× magnification depicting a cutout feature of a catheter.
Figure 3J:
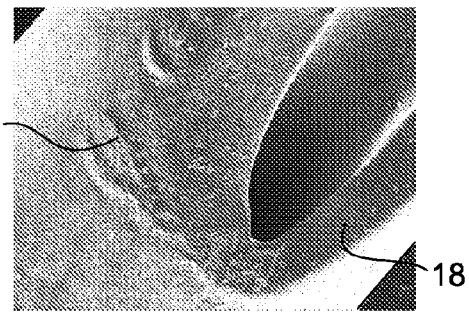
FIG. 3J is an SEM image of a prior art catheter at 96× magnification depicting the cutout and raised surface features of FIG. 3I.
Figure 3K:
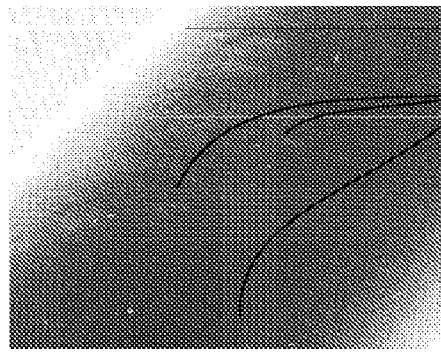
FIG. 3K is an SEM image of a prior art catheter at 94× magnification depicting voids, bumps, striations and other roughness contributors.
Figure 3L:
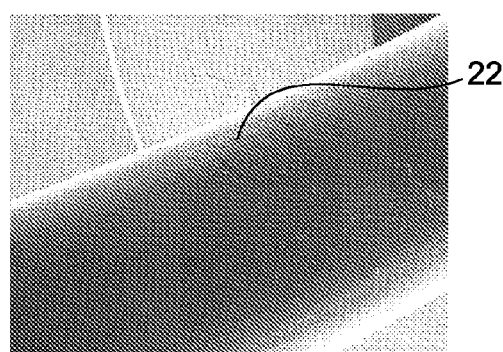
FIG. 3L is an SEM image of a prior art catheter at 46× magnification depicting a wider and more thinly spread surface feature.
Figure 3M:
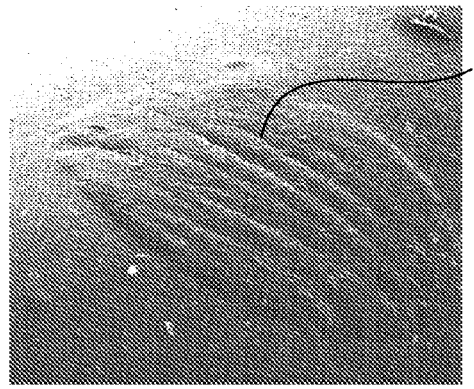
FIG. 3M is an SEM image of a prior art catheter at 227× magnification depicting a close-up view of the wider and more thinly spread surface feature.
Figure 3N:
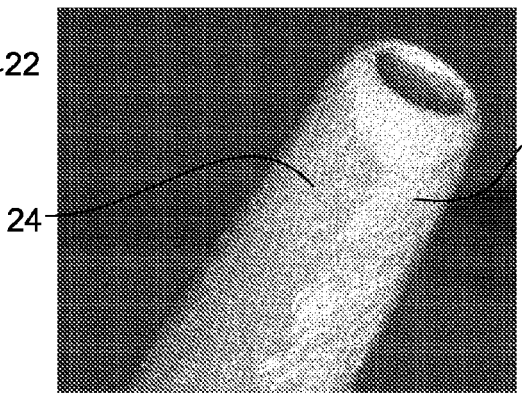
FIG. 3N is an SEM backscatter image of a prior art catheter at 47× magnification depicting material differences or mottle in the tip of a catheter.
Figure 3O:
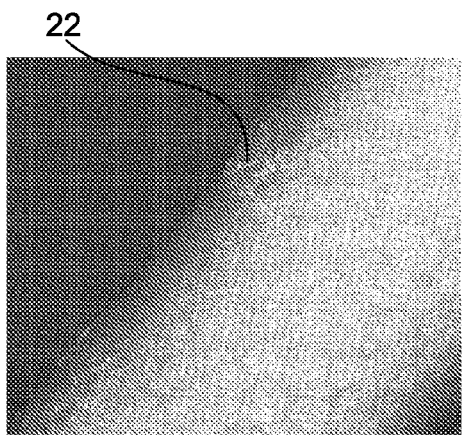
FIG. 3O is an SEM backscatter image of a prior art catheter at 67× magnification depicting close-up view of the material differences or mottle of FIG. 3M.
Figure 3P:
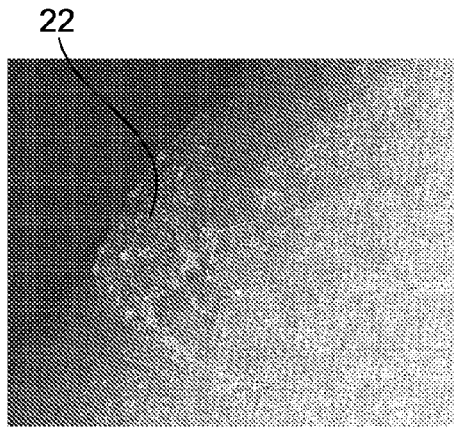
FIG. 3P is an SEM backscatter image of a prior art catheter at 141× magnification depicting the large surface feature of FIG. 3O.
Figure 3Q:
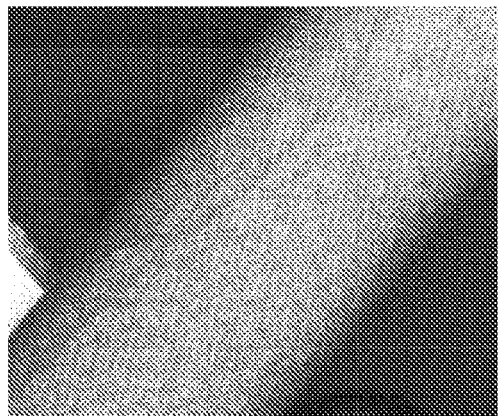
FIG. 3Q is an SEM backscatter image of a prior art catheter at 45× magnification depicting a mottle having small particles with consistent charge properties.
Figure 3R:
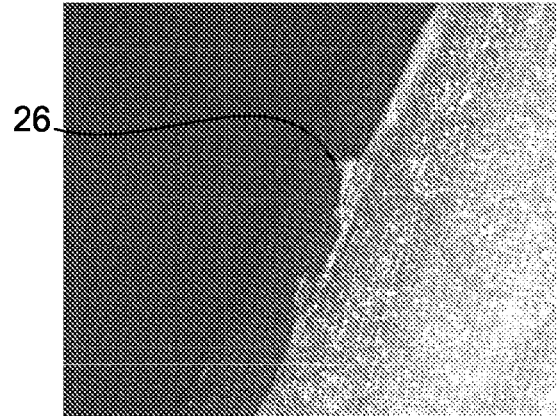
FIG. 3R is an SEM backscatter image of a prior art catheter at 228× magnification depicting a liner like ridge having rough edges and large features.
Figure 3S:
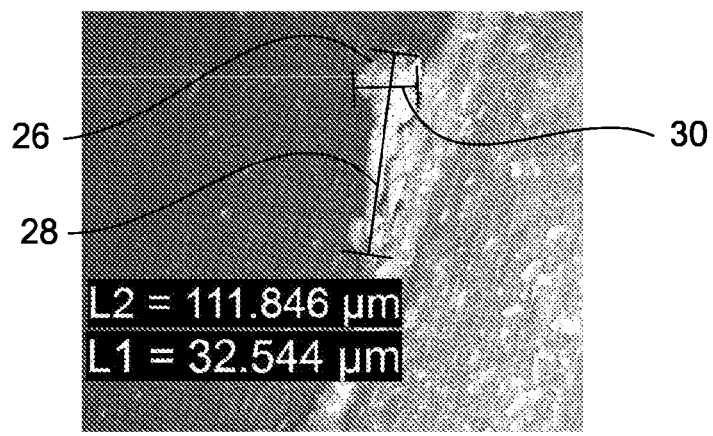
FIG. 3S is an SEM backscatter image of a prior art catheter at 746× magnification depicting a close-up view of the liner like ridge having rough edges and large features of FIG. 3R.

FIGS. 3A-3S are SEM images of a prior art catheter (Arrow International AK-45703-SK). Various surface features and imperfections have been found on external surfaces of the catheter. In capturing the SEM images, the catheter is simply removed from its packaging in its unused condition and disposed under a scanning electron microscope for viewing. Under 20× magnification as depicted in FIG. 3A, the tip 6 of the tubing appears rather smooth. However under higher magnifications as depicted in FIGS. 3B, 3C and 3D, multiple surface roughness morphologies are evident. FIG. 3E is an SEM image of a tip 6 of a prior art catheter depicting multiple surface roughness morphologies and the interface 8 between the tip 6 of a tubing and the tubing 4. The interface 8 appears as a groove about the radial periphery of the catheter 2 and appears to have been caused by imperfections introduced in a fabrication process of the catheter. FIGS. 3F and 3G depict surface ridges 10 on a tubing 4. FIG. 3H is an SEM image of a prior art catheter depicting the raised surface feature 12 having a length 14 of about 60 microns and a width 16 of about 21 microns. FIGS. 3I and 3J depict cutout 18 and raised surface features 12. FIG. 3K depicts voids, bumps, striations 20 and other roughness contributors. FIG. 3L depicts a wider and more thinly spread surface feature 22. FIG. 3M depicts a close-up view of the wider and more thinly spread surface feature 22 of FIG. 3L. FIGS. 3M and 3N are SEM backscatter image of a prior art catheter depicting material differences or mottle 24 in the tip of a catheter. FIGS. 3O and 3P are SEM backscatter images of a prior art catheter depicting a large surface feature 22 of a catheter. FIG. 3Q is an SEM backscatter image of a prior art catheter depicting a mottle 24 having small particles with consistent charge properties. FIGS. 3R and 3S are SEM backscatter images of a prior art catheter depicting a liner like ridge 26 having rough edges and large features, wherein the ridge measures about 112 microns in length 28 and about 33 microns in width 30.

Figure 4A:
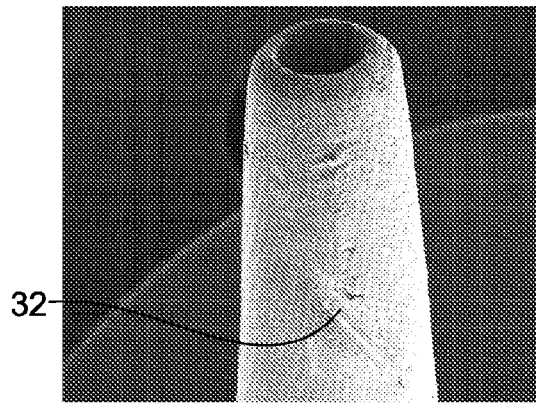
FIG. 4A is an SEM image of a used prior art catheter at 44× magnification depicting a deep abrasion that developed in the tip.
Figure 4B:
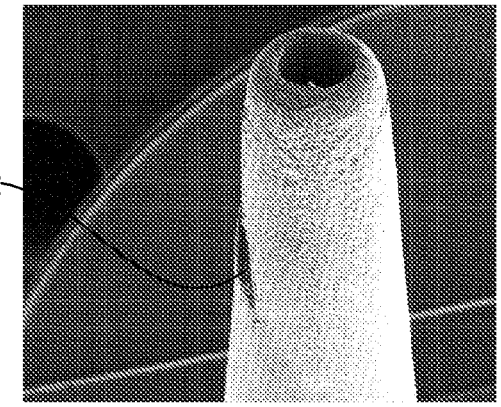
FIG. 4B is an SEM image of another view of the tip of FIG. 4A at 38× magnification depicting the deep abrasion that developed in the tip.
Figure 4C:
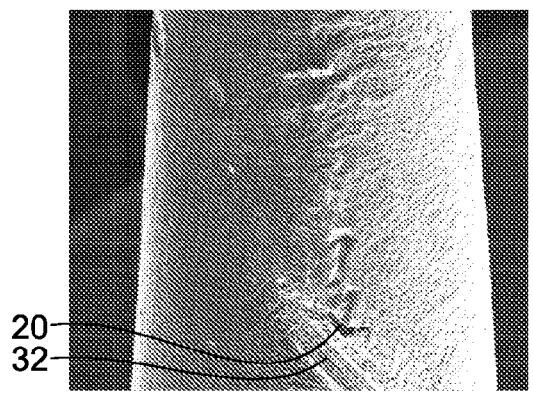
FIG. 4C is an SEM image of yet another view of the tip of FIG. 4A at 89× magnification depicting the deep abrasion that developed in the tip and a void of significant depth.
Figure 4D:
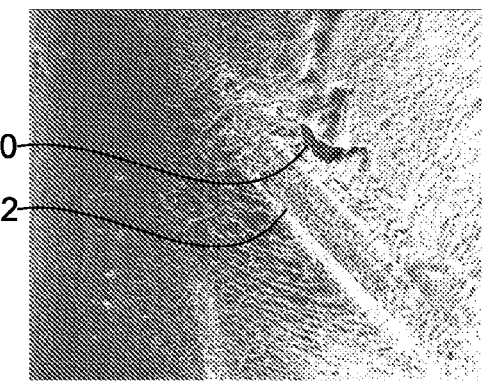
FIG. 4D is an SEM image of yet another view of the tip of FIG. 4A at 138× magnification depicting the deep abrasion that developed in the tip and a void of significant depth.

FIGS. 4A-4M are SEM images of a used prior art catheter. FIGS. 4A and 4B are SEM images of a used prior art catheter depicting a deep abrasion 32 that developed in the tip. FIGS. 4C and 4D are SEM images of yet another view of the tip of FIG. 4A, depicting the deep abrasion 32 that developed in the tip and a void of significant depth.

Figure 4I:
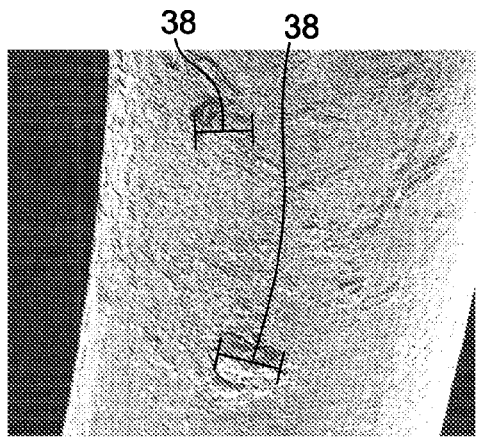
FIG. 4I is an SEM image of a used prior art catheter at 72× magnification depicting surface irregularities of FIG. 4H.
Figure 4J:
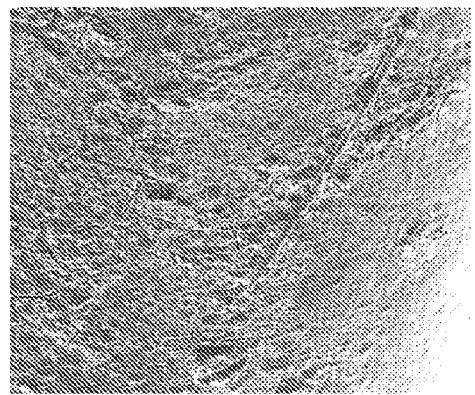
FIG. 4J is an SEM image of a used prior art catheter at 149× magnification depicting additional surface irregularities.
Figure 4K:
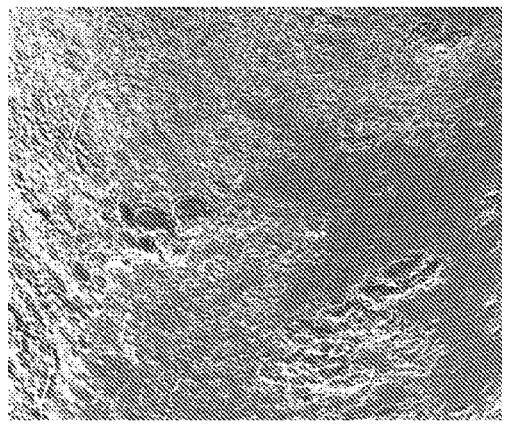
FIG. 4K is an SEM image of a used prior art catheter at 120× magnification depicting additional surface irregularities.
Figure 4L:
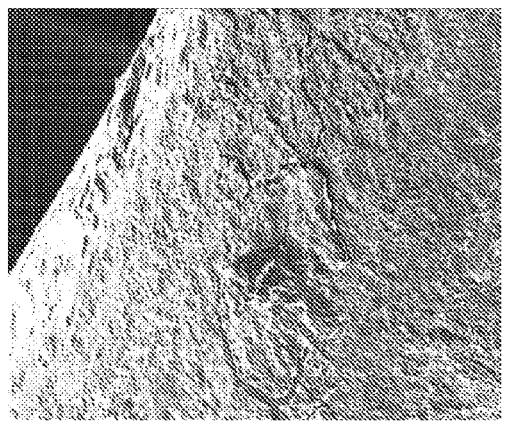
FIG. 4L is an SEM image of a used prior art catheter at 131× magnification depicting additional surface irregularities.
Figure 4M:
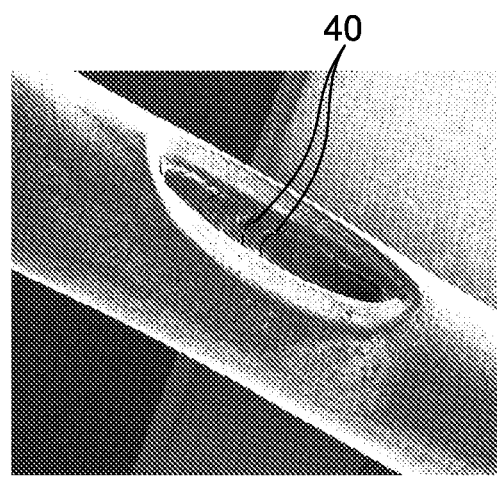
FIG. 4M is an SEM image of a used prior art catheter at 36× magnification depicting a cutout having a cracked cavity.

FIGS. 4E, 4F and 4G depict fiber strands 34 that developed in a tip. FIGS. 4H and 4I depict surface irregularities 36. FIGS. 4J, 4K and 4L depict additional surface irregularities 36 having lengths 38 ranging from about 376 to about 419 microns. FIG. 4M depicts a cutout having a cavity showing cracks 40. Human blood predominantly comprises erythrocytes (red blood cells), leukocytes (white blood cells), platelets, plasma and proteins including fibrin. The size of an erythrocyte particle ranges from about 6 microns to 8 um, i.e., within the order of magnitude of the surface features of prior art catheter. Therefore, such surface features inadvertently aid in attachment of red blood cells on the catheter's surfaces and hence biofilm growth.

Figure 5A:
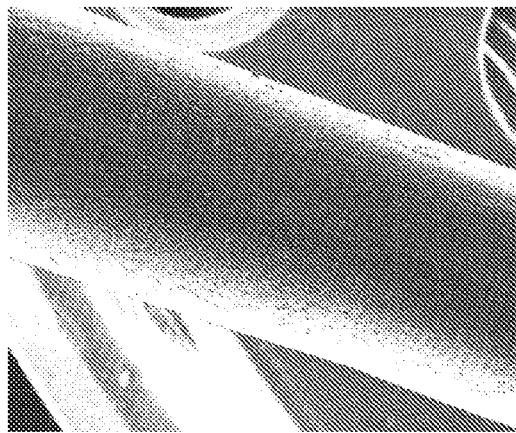
FIG. 5A is an SEM image of sample 1 at 43× magnification depicting busy or rough morphology.
Figure 5B:
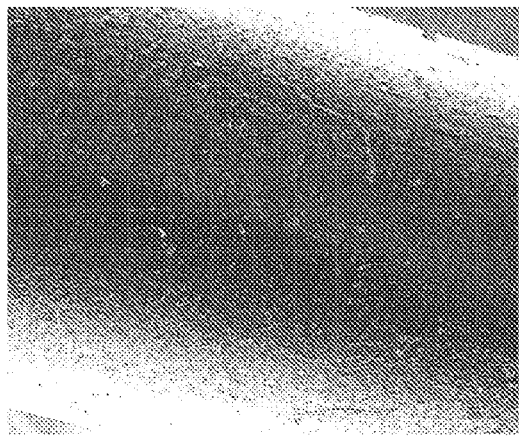
FIG. 5B is an SEM image of the first catheter at 80× magnification depicting busy or rough morphology of FIG. 5A.
Figure 5C:
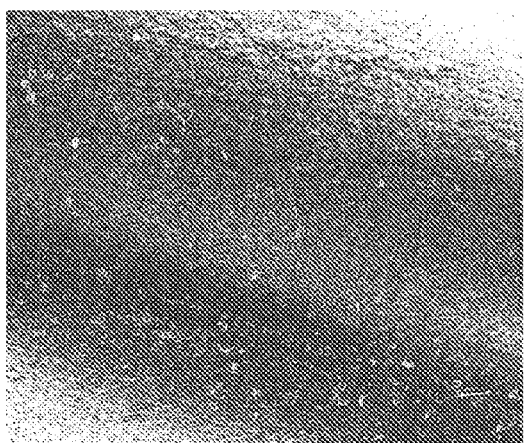
FIG. 5C is another SEM image of sample 1 at 135× magnification depicting busy or rough morphology.
Figure 5D:
FIG. 5D is another SEM image of sample 1 at 227× magnification depicting busy or rough morphology of FIG. 5C.
Figure 5E:
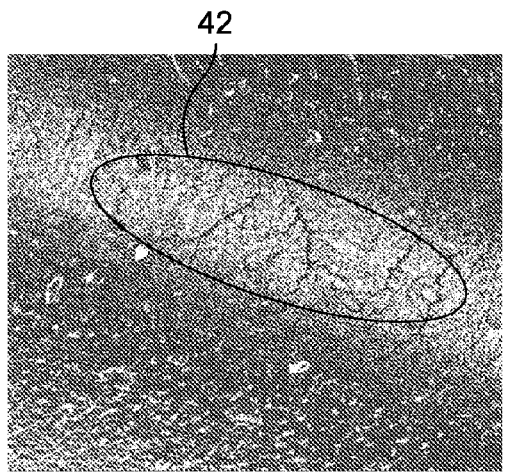
FIG. 5E is another SEM image of sample 1 at 230× magnification depicting fine crazing on some locations of sample 1.
Figure 5F:
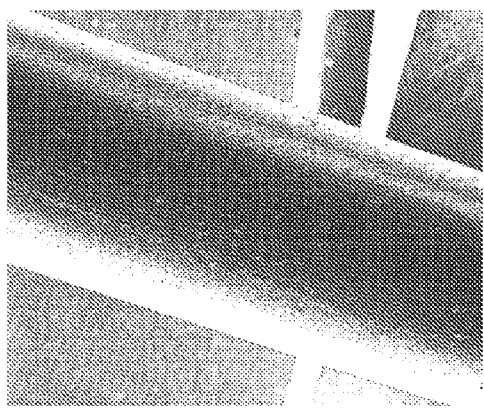
FIG. 5F is an SEM image of sample 2 at 43× magnification depicting busy or rough morphology.
Figure 5G:
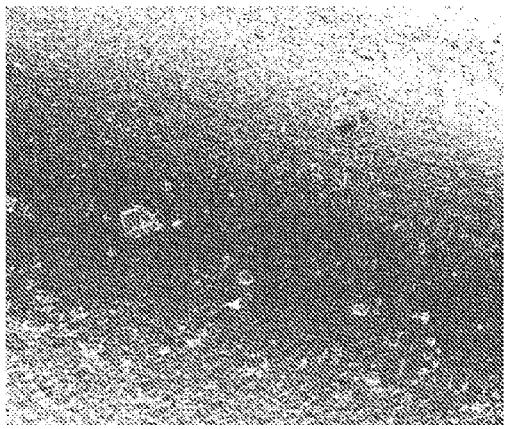
FIG. 5G is an SEM image of sample 2 at 135× magnification depicting busy or rough morphology of FIG. 5F.
Figure 5H:
FIG. 5H is an SEM image of sample 2 at 216× magnification depicting busy or rough morphology of FIG. 5F.
Figure 5I:
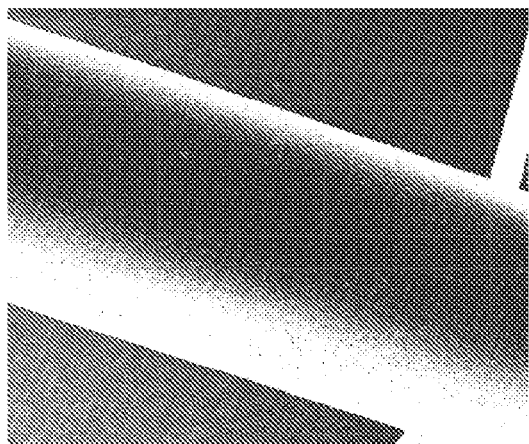
FIG. 5I is an SEM image of sample 3 at 43× magnification depicting a smoother background or reduced roughness and cleaner finish than samples 1 and 2.
Figure 5J:
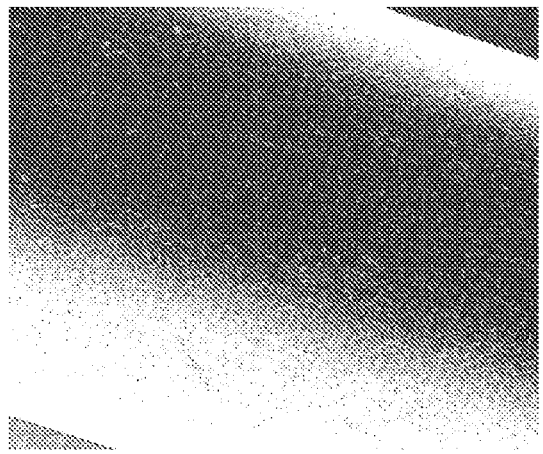
FIG. 5J is an SEM image of sample 3 at 81× magnification depicting a close-up view of FIG. 5I.
Figure 5K:
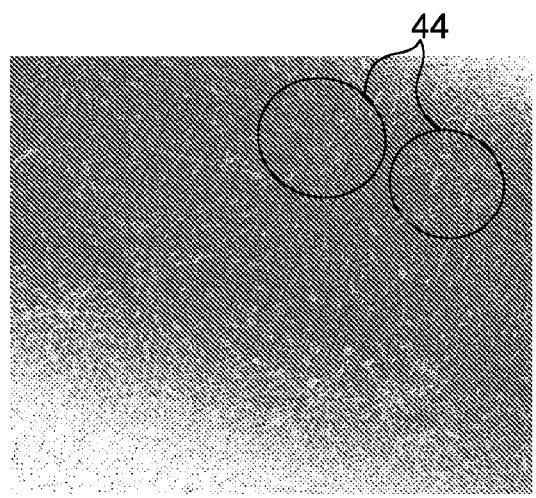
FIG. 5K is an SEM image of sample 3 at 136× magnification depicting fine open structures.
Figure 5L:
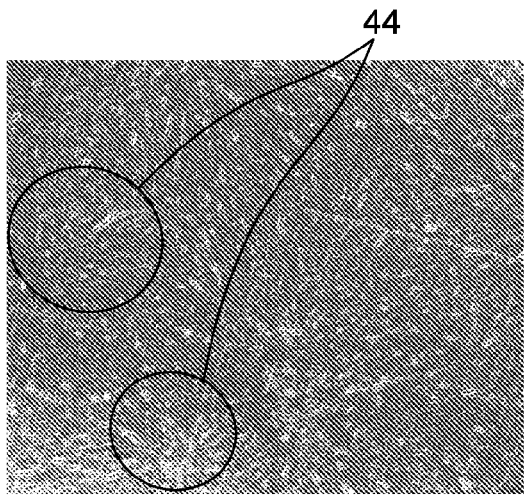
FIG. 5L is an SEM image of sample 3 at 219× magnification depicting a close-up view of FIG. 5K.
Figure 5M:
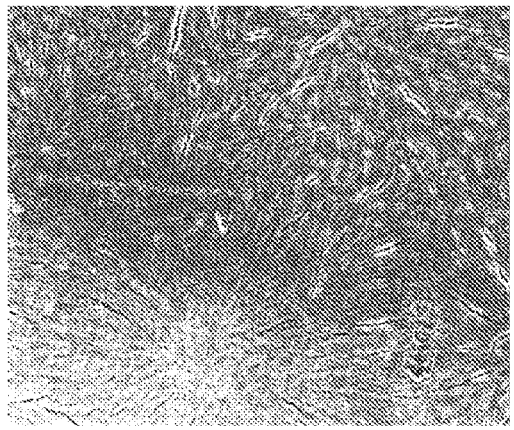
FIG. 5M is an SEM image of sample 3 at 294× magnification depicting a close-up view of FIG. 5K.
Figure 5N:
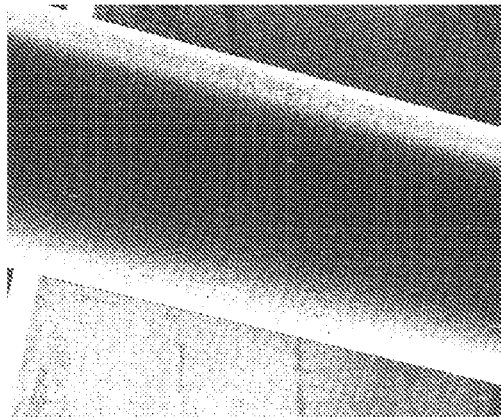
FIG. 5N is an SEM image of sample 4 at 43× magnification depicting a smoother background or reduced roughness and cleaner finish than the samples 1, 2 and 3.
Figure 5O:
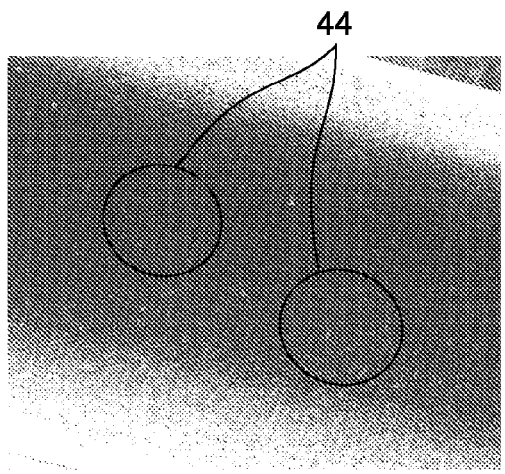
FIG. 5O is an SEM image of sample 4 at 79× magnification depicting a close-up view of FIG. 5N.
Figure 5P:
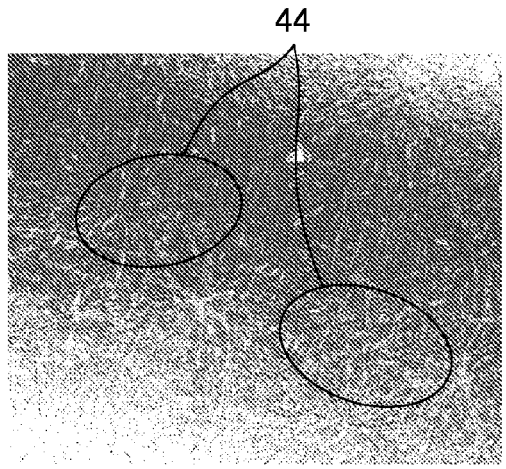
FIG. 5P is an SEM image of sample 4 at 136× magnification depicting fine open structures.
Figure 5Q:
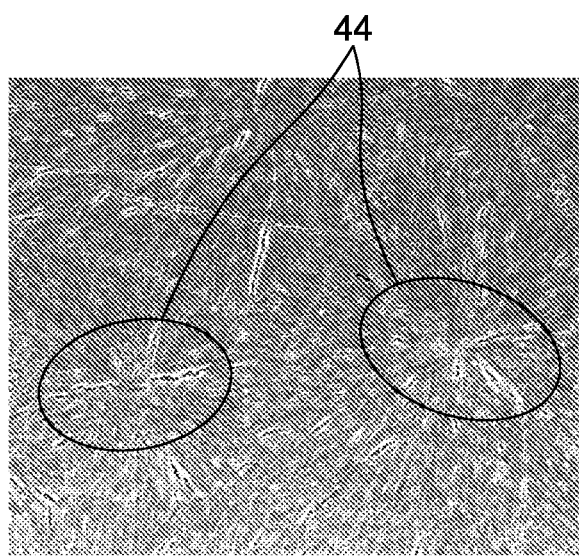
FIG. 5Q is an SEM image of sample 4 at 299× magnification depicting a close-up view of FIG. 5P.

FIGS. 5A-5L represent dry samples 1 or 2 while FIGS. 5M-5Q represent samples 3 and 4. A dry sample is defined as an unused sample. FIGS. 5A-5E are SEM images of sample 1 depicting busy or rough morphology. FIG. 5E is another SEM image of sample 1 depicting fine crazing 42 on some locations of sample 1. FIGS. 5F-5H are SEM images of sample 2 depicting busy or rough morphology. FIG. 5I is an SEM image of sample 3 depicting a smoother background or reduced roughness and cleaner surface finish than samples 1 and 2. FIG. 5J is an SEM image of sample 3 depicting a close-up view of FIG. 5I. FIG. 5K is an SEM image of sample 3 depicting fine open structures 44. FIGS. 5L and 5M are SEM images of sample 3 depicting a close-up view of FIG. 5K. FIG. 5N is an SEM image of sample 4 depicting a smoother background or reduced roughness and cleaner surface finish than samples 1, 2 and 3. FIG. 5O is an SEM image of sample 4 depicting a close-up view of FIG. 5N. FIG. 5P is an SEM image of sample 4 depicting fine open structures 44. FIG. 5Q is an SEM image of sample 4 depicting a close-up view of FIG. 5P. Although appeared smooth in FIGS. 5I and 5N, samples 3 and 4 evidently comprise imperfections as shown at higher magnifications.

Figure 6A:
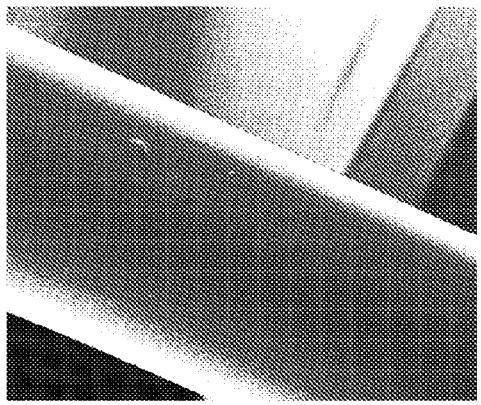
FIG. 6A is an SEM image of an uncoated polyurethane catheter at 43× magnification depicting a relatively smooth surface that is free from surface roughness, irregularities, voids, bumps, ridges, fiber strands, etc.
Figure 6B:
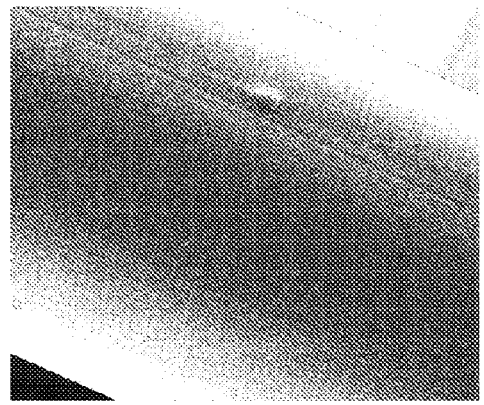
FIG. 6B is an SEM image of the uncoated polyurethane catheter at 80× magnification depicting a close-up view of FIG. 6A.
Figure 6C:
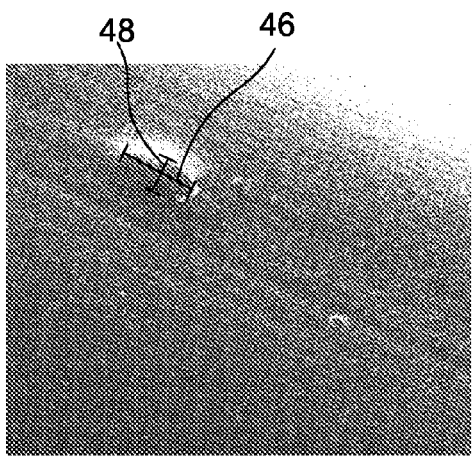
FIG. 6C is an SEM image of the uncoated polyurethane catheter at 227× magnification depicting a raised surface feature.
Figure 6D:
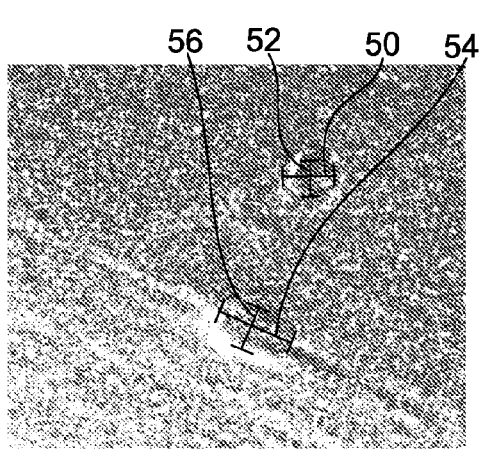
FIG. 6D is an SEM image of the uncoated polyurethane catheter at 704× magnification depicting raised surface features.
Figure 6E:
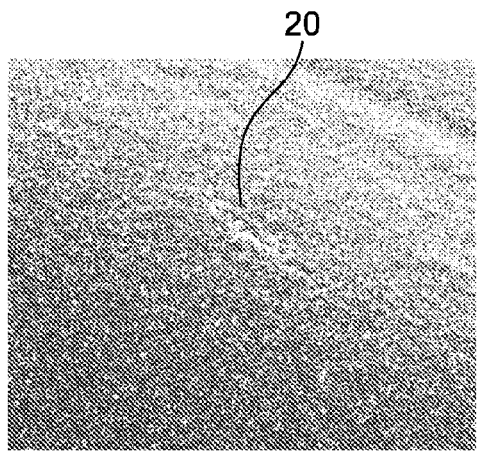
FIG. 6E is an SEM image of the uncoated polyurethane catheter at 454× magnification depicting an elongate void.
Figure 6F:
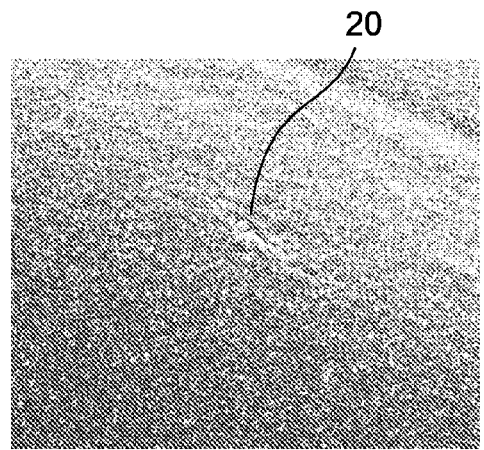
FIG. 6F is an SEM image of the uncoated polyurethane catheter at 759× magnification depicting the elongate void of FIG. 6E.

FIGS. 6A and 6B are SEM images of a dry sample 5 or uncoated polyurethane catheter, depicting a relatively smooth surface that is free from surface roughness, irregularities, voids, bumps, ridges, fiber strands, etc. FIG. 6C is an SEM image of the uncoated polyurethane catheter depicting a raised surface feature having a length 46 of about 154 microns and a width 48 of about 68 microns. FIG. 6D is an SEM image of the uncoated polyurethane catheter, depicting raised surface features. One raised feature measures about 32 microns in length 50 and about 27 microns in width 52. Another raised feature measures about 53 microns in length 54 and about 38 microns in width 56. FIGS. 6E and 6F depict an elongate void 20. Although the relatively smooth nature of the surface appears to be a promising candidate for anti-biofilm materials, a wet test revealed otherwise as demonstrated elsewhere herein.

Figure 7A:
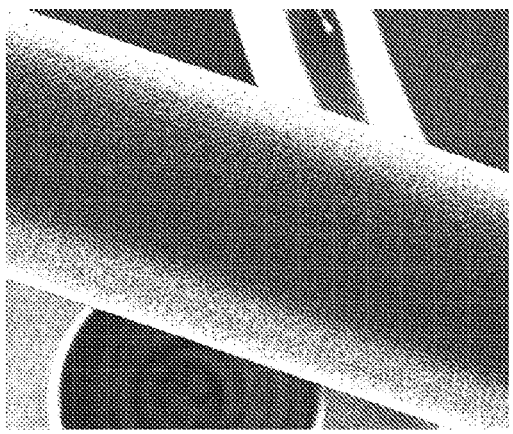
FIG. 7A is an SEM image of the post wet test sample 1 at 43× magnification depicting a relatively uniform surface that is free from large raised surface features, irregularities, voids, bumps, fiber strands, etc.
Figure 7B:
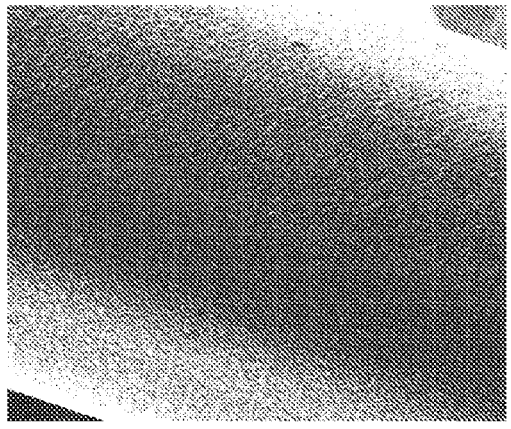
FIG. 7B is an SEM image of the post wet test sample 1 at 80× magnification depicting a close-up view of surface features of FIG. 7A.
Figure 7C:
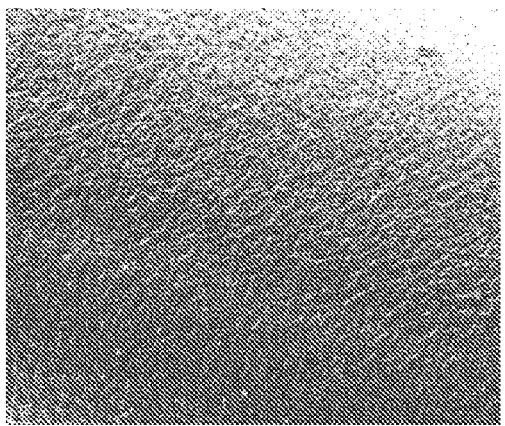
FIG. 7C is an SEM image of the post wet test sample 1 at 135× magnification depicting a close-up view of surface features of FIG. 7A.
Figure 7D:
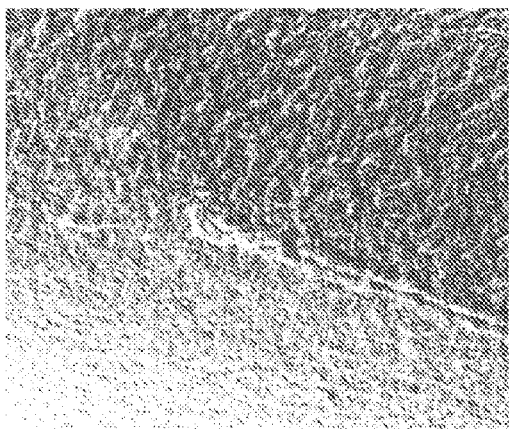
FIG. 7D is an SEM image of the post wet test sample 1 at 231× magnification depicting a close-up view of surface features of FIG. 7A.
Figure 7E:
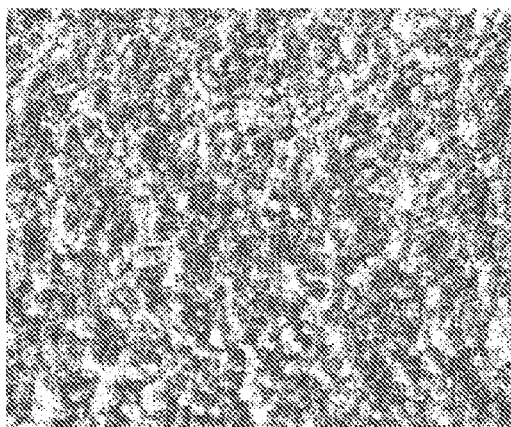
FIG. 7E is an SEM image of the post wet test sample 1 at 606× magnification depicting a close-up view of surface features of FIG. 7A that are void of sharp or jagged textures.
Figure 7F:
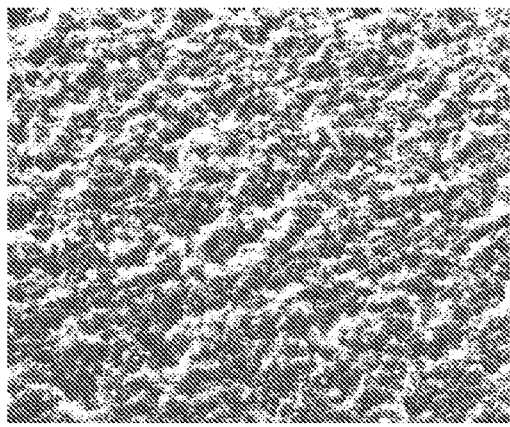
FIG. 7F is an SEM image of the post wet test sample 1 at 602× magnification depicting a close-up view of surface features of FIG. 7A that are void of sharp or jagged textures.
Figure 7G:
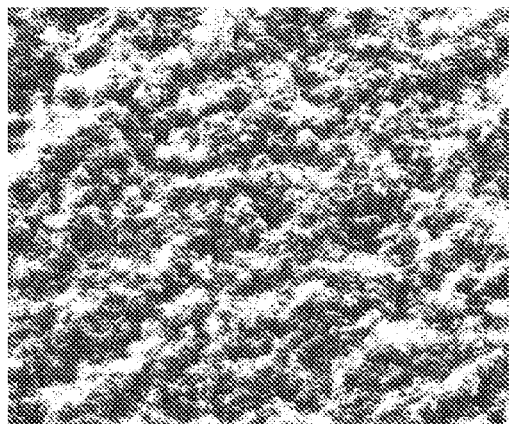
FIG. 7G is an SEM image of the post wet test sample 1 at 1000× magnification depicting a close-up view of surface features of FIG. 7A that are void of sharp or jagged textures.
Figure 7H:
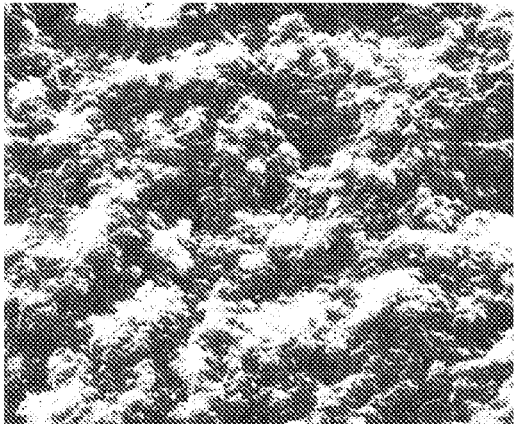
FIG. 7H is an SEM image of the post wet test sample 1 at 2010× magnification depicting a close-up view of surface features of FIG. 7A that are void of sharp or jagged textures.

FIGS. 7A-7C are SEM images of the post wet test sample 1 depicting a relatively uniform surface that is free from large raised surface features, irregularities, voids, bumps, fiber strands, etc. FIG. 7D depicts a close-up view of surface features of FIG. 7A. FIGS. 7E-7H are SEM images of the post wet test sample 1, depicting a close-up view of surface features of FIG. 7A that are void of sharp or jagged textures. Although relatively free from abrupt surface features, sample 1 displays relatively predictable texture when wet. It is evident that sample 1 is devoid of adherent blood components when wet.

Figure 8A:
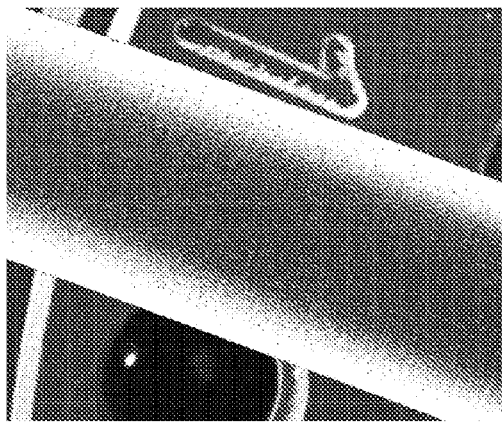
FIG. 8A is an SEM image of the post wet test sample 3 at 43× magnification depicting a normal roughness distribution with a population of proud particles.
Figure 8B:
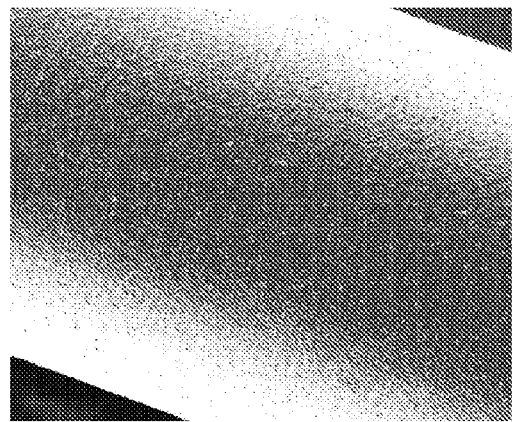
FIG. 8B is an SEM image of the post wet test sample 3 at 79× magnification depicting a close-up view of surface features of FIG. 8A.

FIGS. 8A and 8B are SEM images of the post wet test sample 3 at lower magnifications, depicting a normal roughness distribution with a population of proud particles 70.

Figure 8C:
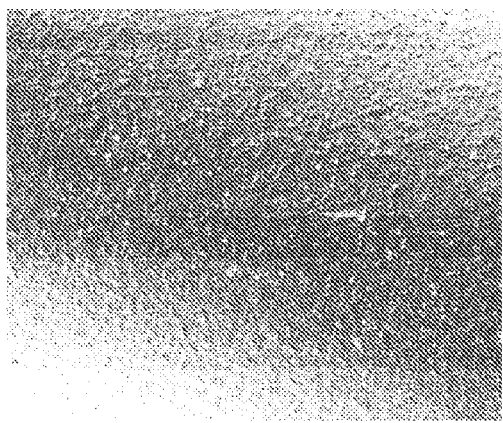
FIG. 8C is an SEM image of the post wet test sample 3 at 135× magnification depicting a close-up view of proud particles of FIG. 8A.
Figure 8D:
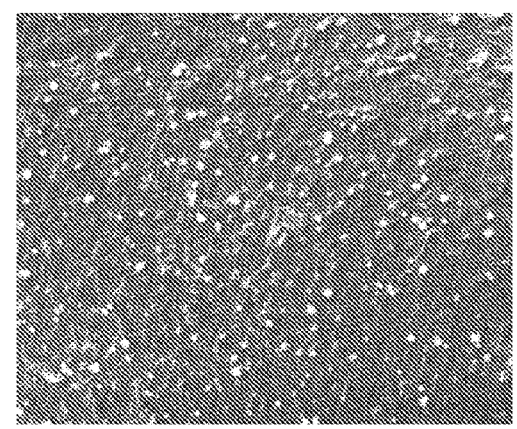
FIG. 8D is an SEM image of the post wet test sample 3 at 294× magnification depicting a close-up view of proud particles of FIG. 8A.
Figure 8E:
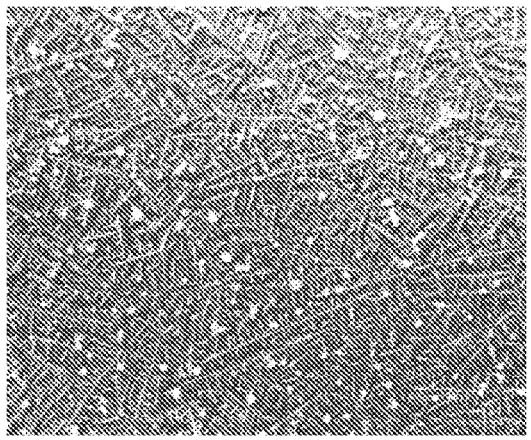
FIG. 8E is an SEM image of the post wet test sample 3 at 304× magnification depicting a close-up view of proud particles and crystalline structures of FIG. 8A.
Figure 8F:
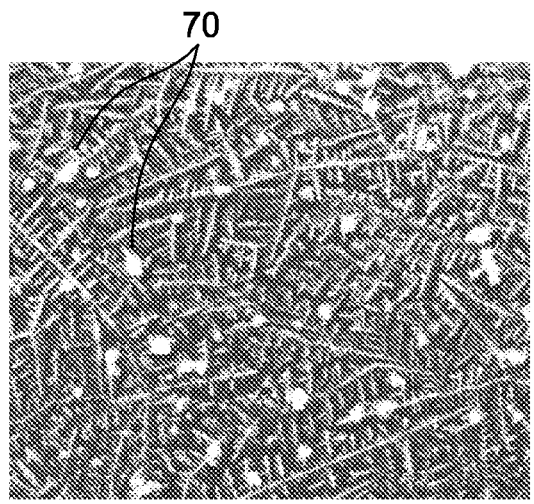
FIG. 8F is an SEM image of the post wet test sample 3 at 597× magnification depicting a close-up view of proud particles and crystalline structures of FIG. 8A.
Figure 8G:
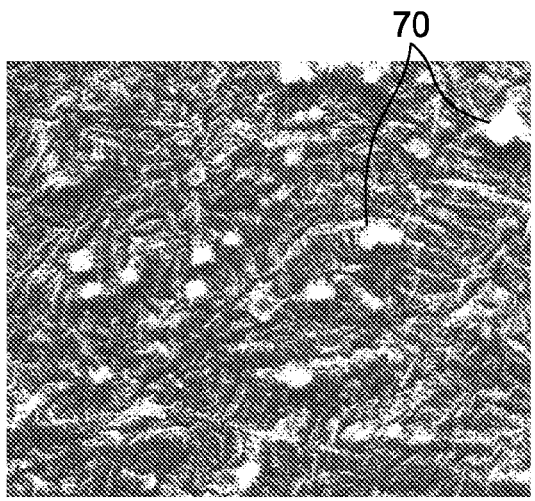
FIG. 8G is an SEM image of the post wet test sample 3 at 1010× magnification depicting a close-up view of proud particles and crystalline structures of FIG. 8A.
Figure 8H:
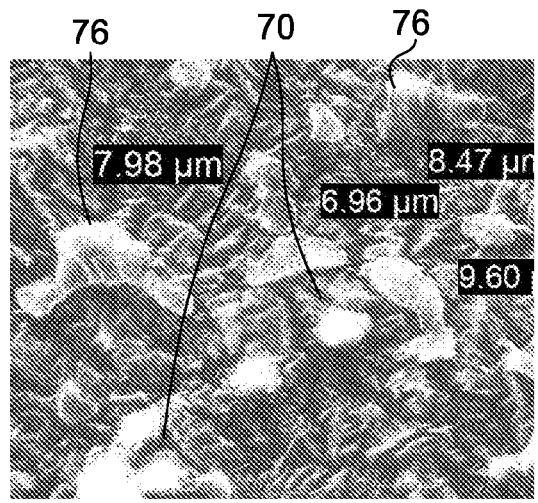
FIG. 8H is an SEM image of the post wet test sample 3 at 2000× magnification depicting a close-up view of proud particles and crystalline structures of FIG. 8A.

Although the surface appears to be rather consistent and devoid of abrupt surface features at such magnifications, the surface appears to have light colored particles consistently dispersed on the entire surface of wet sample 3 at higher magnifications. FIGS. 8C and 8D are SEM images of the post wet test sample 3 at higher magnifications, depicting a close-up view of proud particles 70 of FIG. 8A. At higher magnifications as disclosed in FIGS. 8E and 8F, proud particles and crystalline structures appear more prominent. At even higher magnifications as disclosed in FIGS. 8G and 8H, the proud particles 70 appear to be red blood cells. Irregular shaped features 76 range from about 6 microns to about 10 microns which are similar in size to leukocytes. The proud particles appear to measure about 6 microns which are similar in size to red blood cells.

Figure 9A:
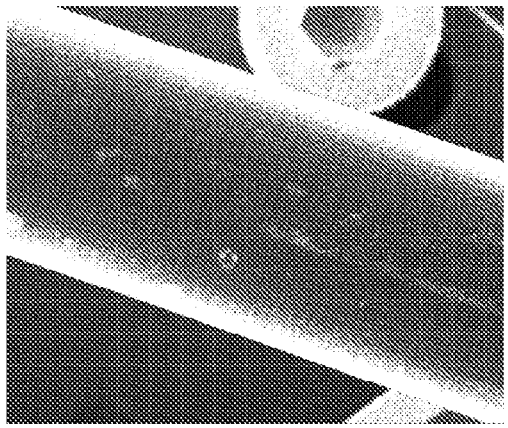
FIG. 9A is an SEM image of the post wet test uncoated polyurethane tubing at 44× magnification depicting surface deposits on portions of the catheter.
Figure 9B:
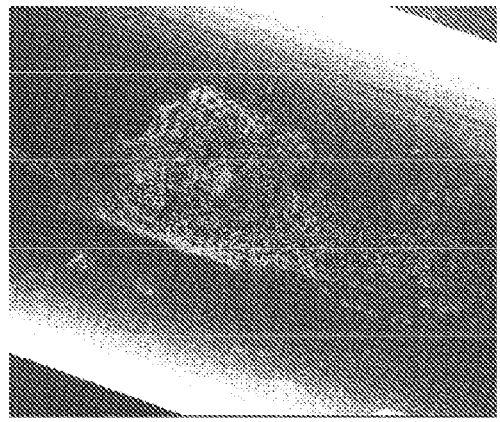
FIG. 9B is an SEM image of the post wet test uncoated polyurethane tubing at 81× magnification depicting a close-up view of FIG. 9A.
Figure 9C:
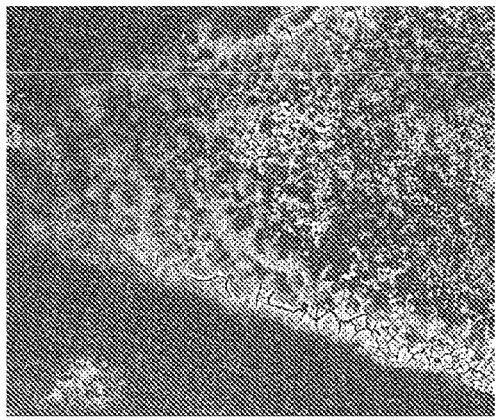
FIG. 9C is an SEM image of the post wet test uncoated polyurethane tubing at 230× magnification depicting a close-up view of surface deposits with multiple signatures/morphologies of FIG. 9A.
Figure 9D:
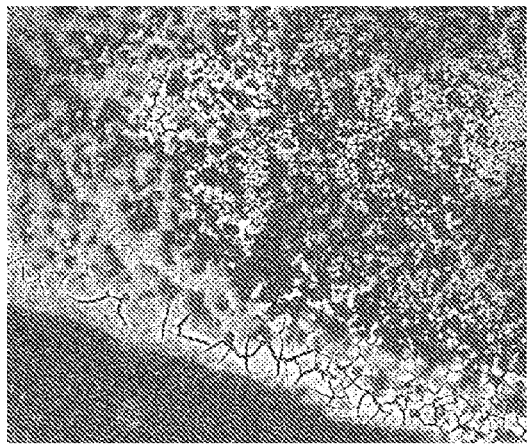
FIG. 9D is an SEM image of the post wet test uncoated polyurethane tubing at 300× magnification depicting a close-up view of surface deposits with multiple signatures/morphologies of FIG. 9A.
Figure 9E:
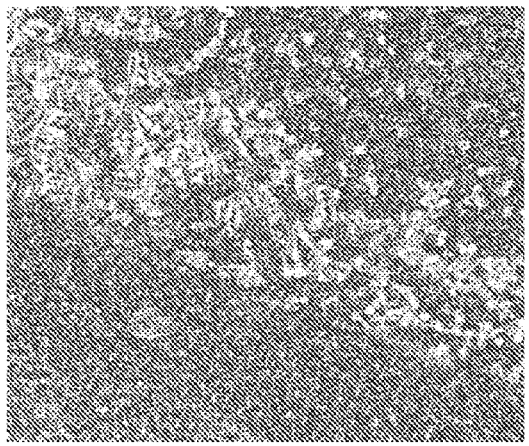
FIG. 9E is an SEM image of the post wet test uncoated polyurethane tubing at 501× magnification depicting a close-up view of surface deposits with multiple signatures/morphologies of FIG. 9A.
Figure 9F:
FIG. 9F is an SEM image of the post wet test uncoated polyurethane tubing at 362× magnification depicting a close-up view of surface deposits with multiple signatures/morphologies of FIG. 9A.
Figure 9G:
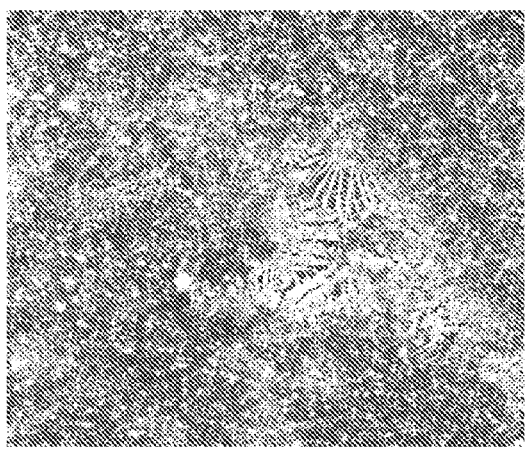
FIG. 9G is an SEM image of the post wet test uncoated polyurethane tubing at 1030× magnification depicting a close-up view of break down of surface structure of FIG. 9A.
Figure 9H:
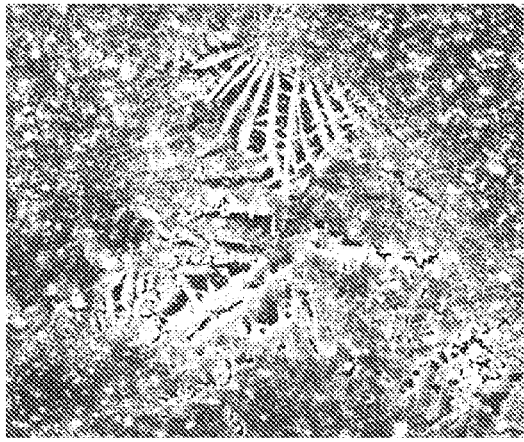
FIG. 9H is an SEM image of the post wet test uncoated polyurethane tubing at 2080× magnification depicting a close-up view of break down of surface structure of FIG. 9A.

FIGS. 9A and 9B are SEM images of the post wet test uncoated polyurethane tubing, depicting surface deposits on portions of the tubing. FIGS. 9C-9F depict close-up views of surface deposits with multiple signatures/morphologies of FIG. 9A. FIGS. 9G and 9H depict close-up views of break down of surface structure of FIG. 9A. Such imperfections again provide opportunities for adherent blood components. FIG. 9I is an SEM image of the post wet test uncoated polyurethane tubing depicting a close-up view of collection of red blood cells 72 on its surface. At even higher magnification, FIG. 9J depicts a close-up view of collection of red blood cells 72 on the uncoated polyurethane tubing.

As demonstrated in the wet tests disclosed elsewhere herein, the first surface as in samples 1 or 2, appears to be free or nearly free from one or more adherent blood components. It shall also be apparent that although a surface may appear smooth in dry condition, a wet test may reveal surface features not readily apparent in the dry condition. Samples 3, 4 and 5, which appear smooth under low magnification and/or in dry condition, unexpectedly attract tremendous amounts of adherent blood components. In contrast, samples 1 and 2, which appear to have rougher surface profile cause unexpectedly low amounts or void of adherent blood components.

As such, Applicant has discovered an optimal surface profile for use in a luminal system in vivo. Samples 1 and 2 may be constructed from polyurethane or another suitable polymer such as polyethylene and healthcare silicone. In one embodiment, the suitable surface may be formed integrally with its substrate tubing. In another embodiment, a coating of polyurethane or polyethylene particles may be applied to surfaces of a substrate tubing via spraying, dipping or electrostatic coating. In yet another embodiment, surfaces of a substrate tubing can be polished to achieve a similar result.

Figure 10:
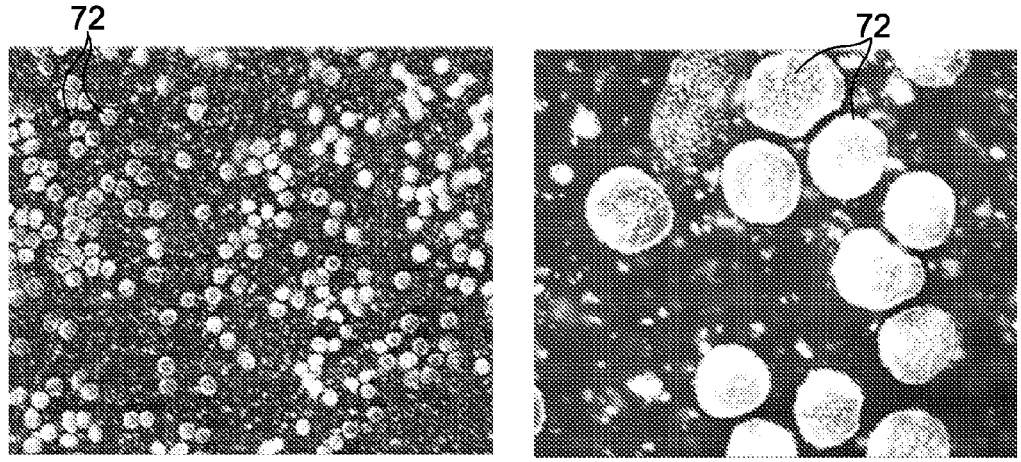
FIG. 10 is a table depicting roughness profile parameters of dry sample 5, wet samples 1 and 3.
Figure 11:
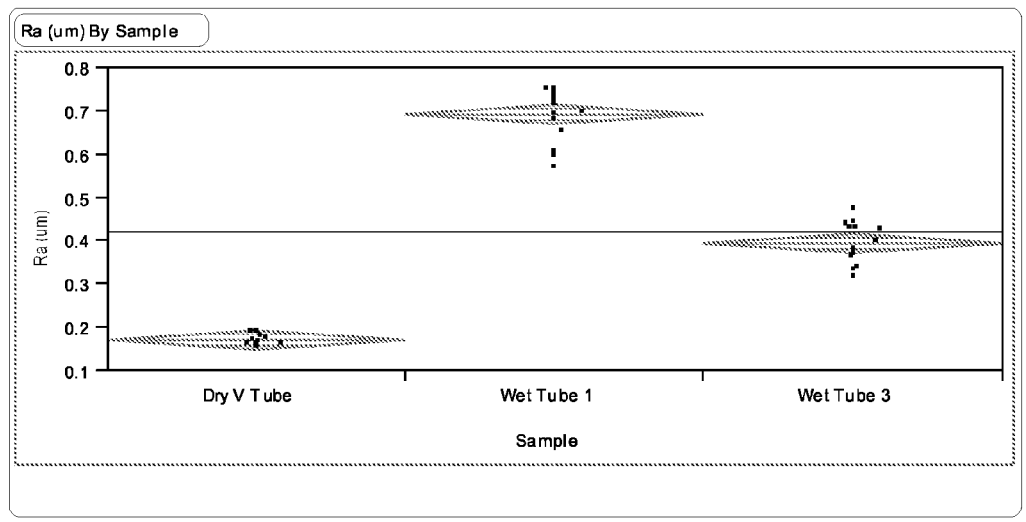
FIG. 11 is a chart depicting Ra values of dry sample 5, wet samples 1 and 3.
Figures 12, 13:
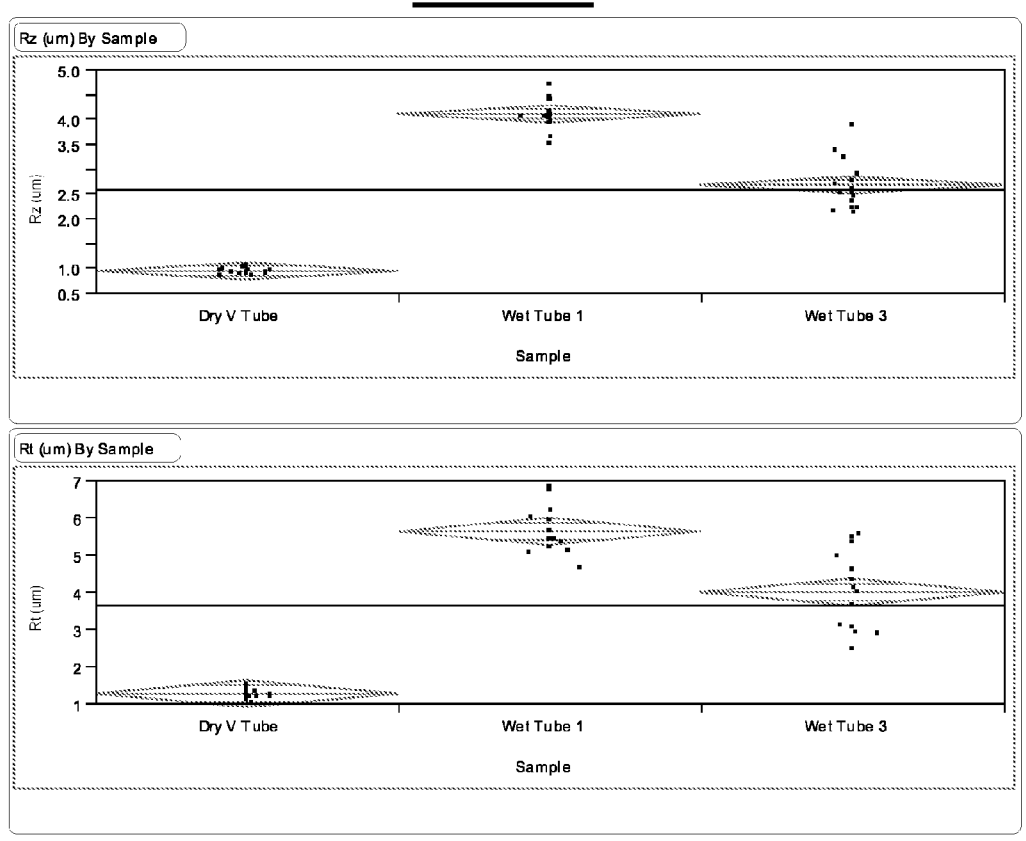
FIG. 12 is a chart depicting Rz values of dry sample 5, wet samples 1 and 3.
FIG. 13 is a chart depicting Rt values of dry sample 5, wet samples 1 and 3.

FIGS. 10-13 depict profile analysis of fifteen surface profiles of dry sample 5, wet samples 1 and 3, where each surface profile of 1.4 mm in length is taken from each sample, analyzed and averaged. FIG. 10 is a chart depicting roughness profile parameters of dry sample 5, wet samples 1 and 3. FIG. 11 is a chart depicting Ra values of dry sample 5, wet samples 1 and 3. FIG. 12 is a chart depicting Rz values of dry sample 5, wet samples 1 and 3. FIG. 13 is a chart depicting Rt values of dry sample 5, wet samples 1 and 3. Measurements were performed on dry sample 5, wet samples 1 and 3 using an interferometric microscope. The surfaces are contrasted in terms of Ra, Rz, Rt and Sm values. A standard deviation (Std. Dev.) is further included for each profile parameter of each sample. Among the three surfaces of dry sample 5, wet samples 1 and 3, wet sample 1 possesses profile parameters indicating more severe roughness than other samples as easily discernible from FIGS. 11-13. For instance, the Ra, Rz and Rt values of wet sample 1 are significantly higher than dry sample 5 and wet sample 3. As an example, wet sample 1 has an Ra value of 0.694, which is significantly higher the Ra value of 0.173 for dry sample 5 and 0.397 for wet sample 3. Referring back to Bourassa, where it was stated that:

"They stress the need for high quality catheter materials with smooth and regular surface in the prevention of thromboembolic complications from coronary arteriography."

If a profile had been selected from among the three profiles based on it being "smooth and regular," dry sample 5 would have been the most preferred choice, followed by wet sample 3. A selection of an anti-biofilm surface based on these roughness values, i.e., Ra, Rz and Rt values, alone would lead to the selection of dry sample 5 over wet samples 3 and 1. However, as will be apparent from FIG. 14 that area statistics must be examined to further determine the optimal anti-biofilm surface in conjunction with observations from the SEMs as demonstrated in FIGS. 3A-9J.

FIG. 14 is a table contrasting area statistics of dry sample 5, wet samples 1 and 3. FIGS. 16-21 show area statistics from three locations on each sample. The surfaces are contrasted in terms of Ra, Rq, Rsk, Rku, Rz, Rpk, Rk and Rvk. The area statistics of FIG. 14 were performed on each sample at 40× magnification. Sample 1 comprises a distinct range of skewness (or Rsk) values of from about −0.01 to about −0.6. Sample 1 further differs distinctly from sample 3 with respect to kurtosis (or Rku). Sample 1 comprises a kurtosis value ranging from about 2.7 to about 3.3 while sample 3 comprises a kurtosis value ranging from about 5.0 to about 16.0. Therefore, although sample 3 appears to be significantly smoother according to the roughness parameters disclosed in FIGS. 10-13, the kurtosis value depicts a surface having extreme peaks and/or valleys which may have contributed to its affinity for red blood cells and other blood components.

Figure 15:
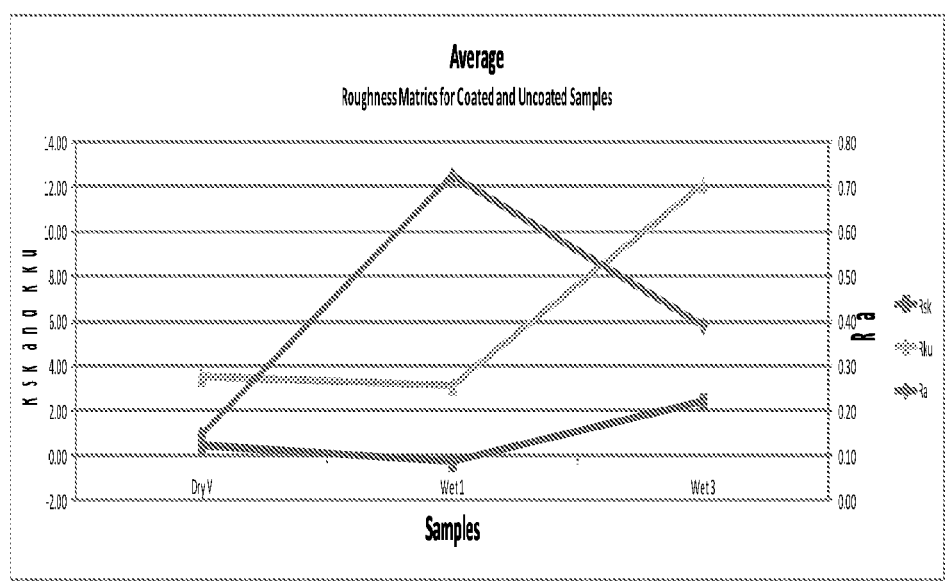
FIG. 15 is a chart contrasting surface profile properties of dry sample 5, wet samples 1 and 3 in terms of Rsk, Rku and Ra.

FIG. 15 is a chart contrasting surface profile properties of dry sample 5, wet samples 1 and 3 in terms of Rsk, Rku and Ra. The profile parameters of samples from area statistics of FIG. 14 are averaged to produce the results in FIG. 15. For instance, the kurtosis value of wet sample 3 of 12.12 is obtained by averaging the samples of 5.359, 15.017 and 15.994. It is therefore apparent from this chart that wet sample 1 possesses significantly different Rsk and Ra from other samples.

Figure 16:
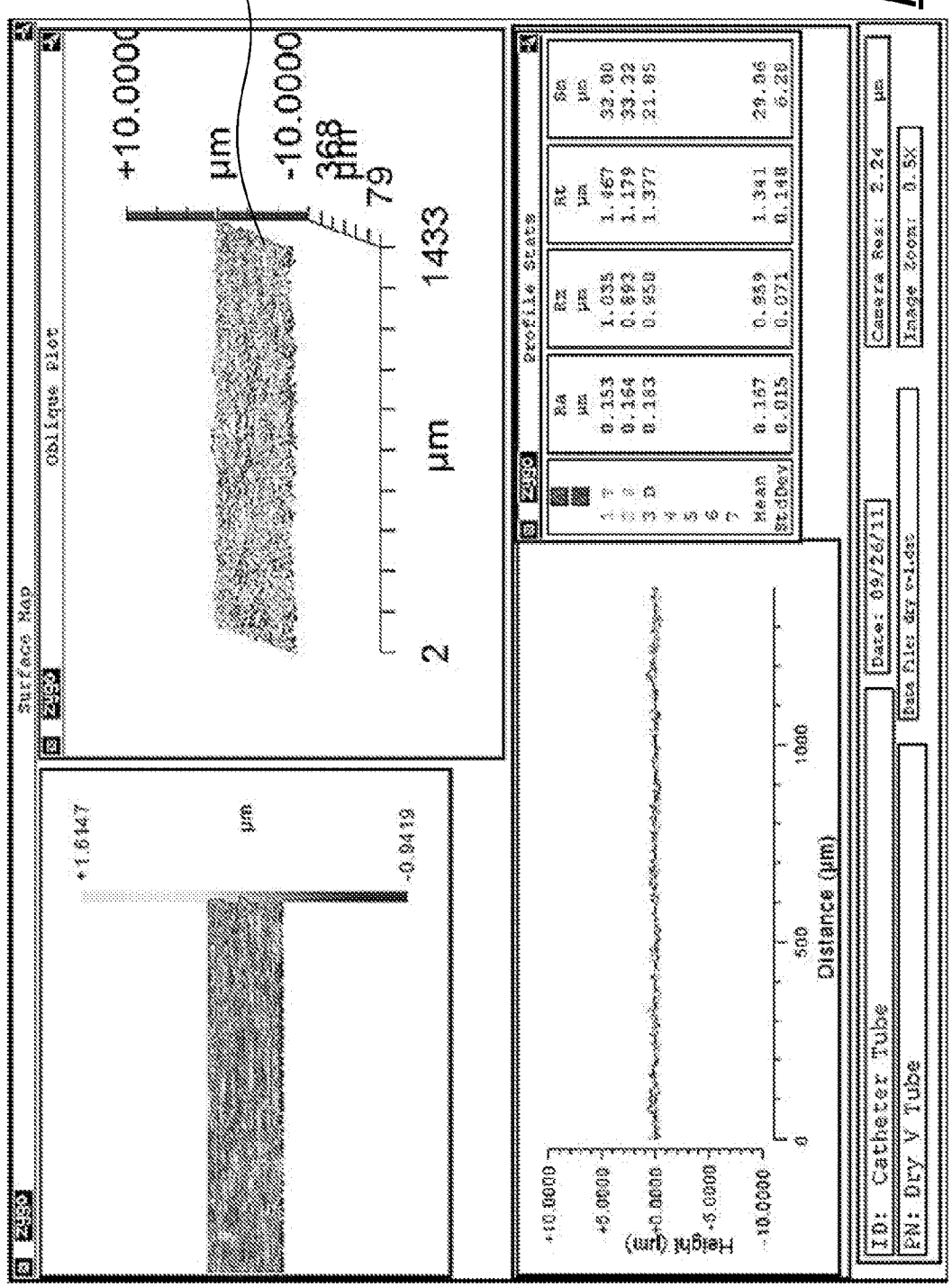
FIG. 16 depicts a surface scan at 5× magnification of dry sample 5.
Figure 17:
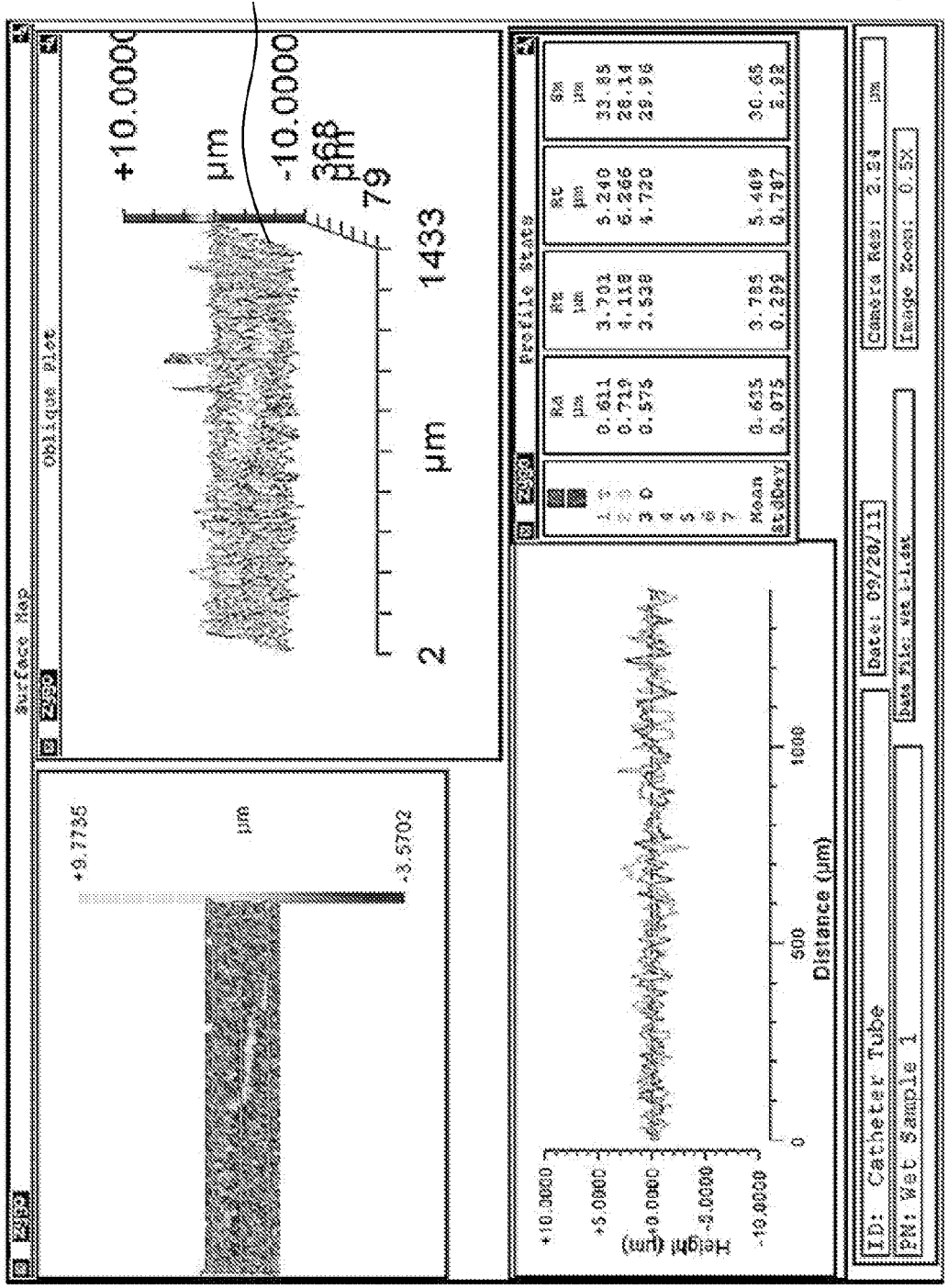
FIG. 17 depicts a surface scan at 5× magnification of wet sample 1.
Figure 18:
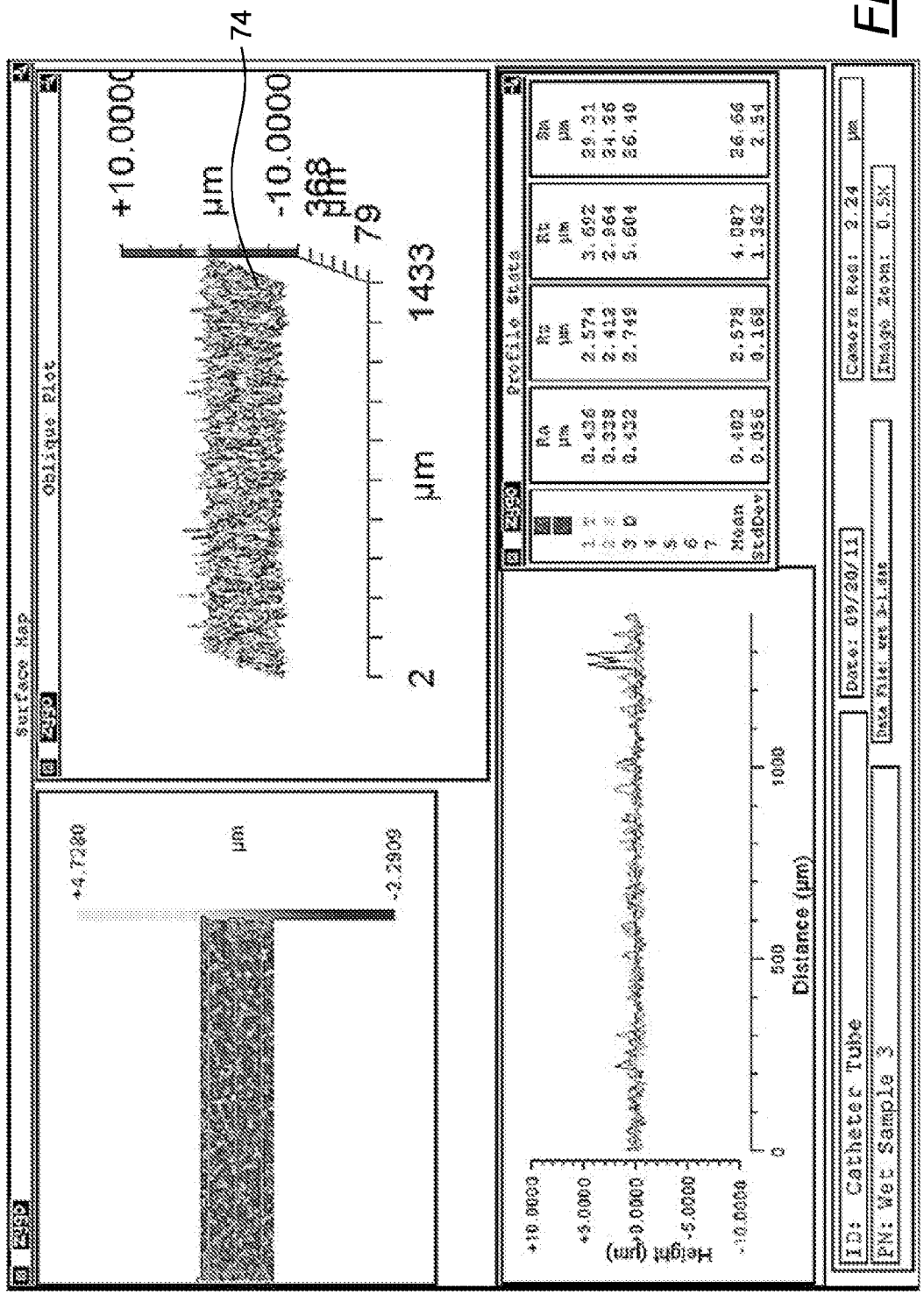
FIG. 18 depicts a surface scan at 5× magnification of wet sample 3.
Figure 19:
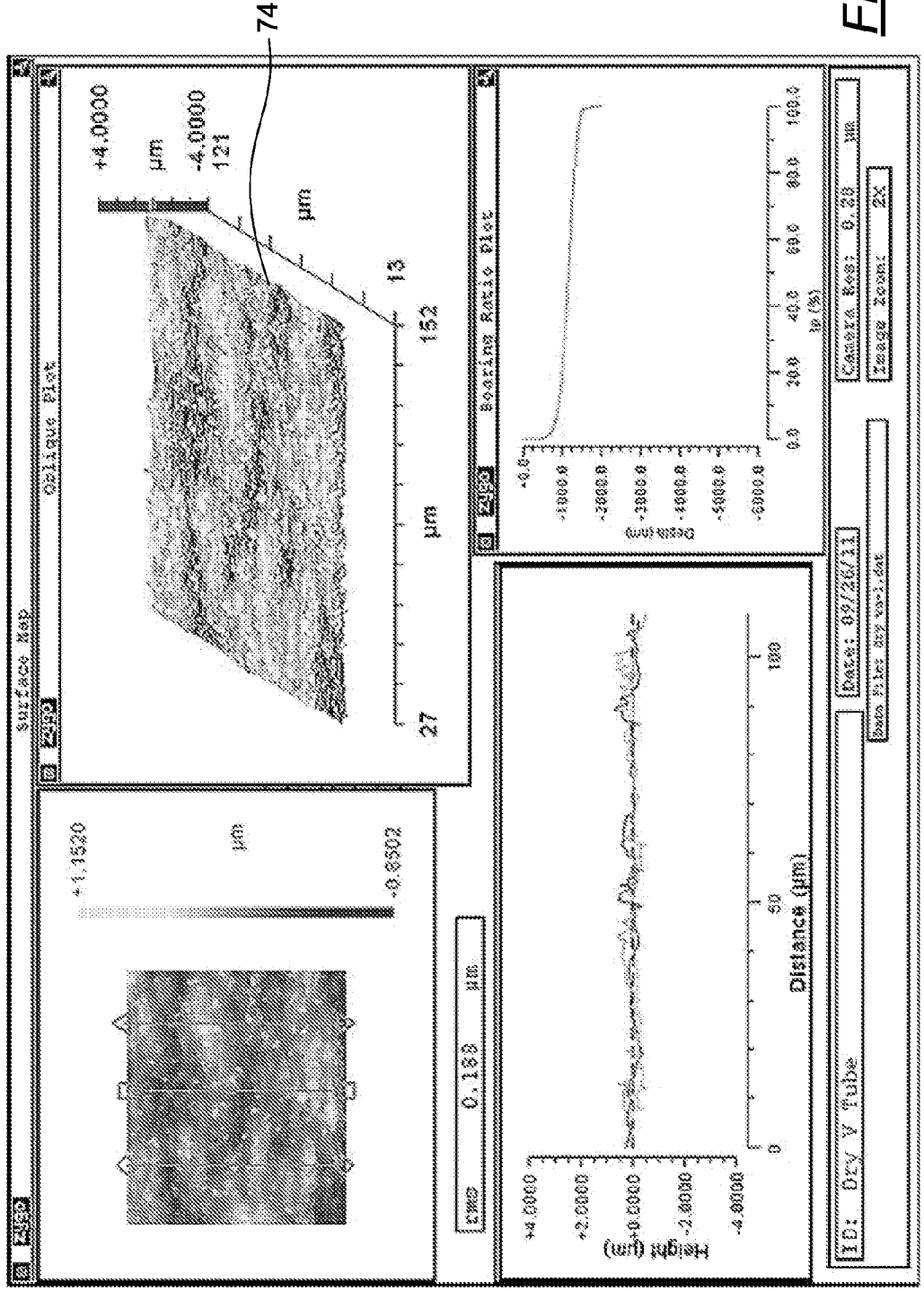
FIG. 19 depicts a surface scan at 40× magnification of dry sample 5.
Figure 20:
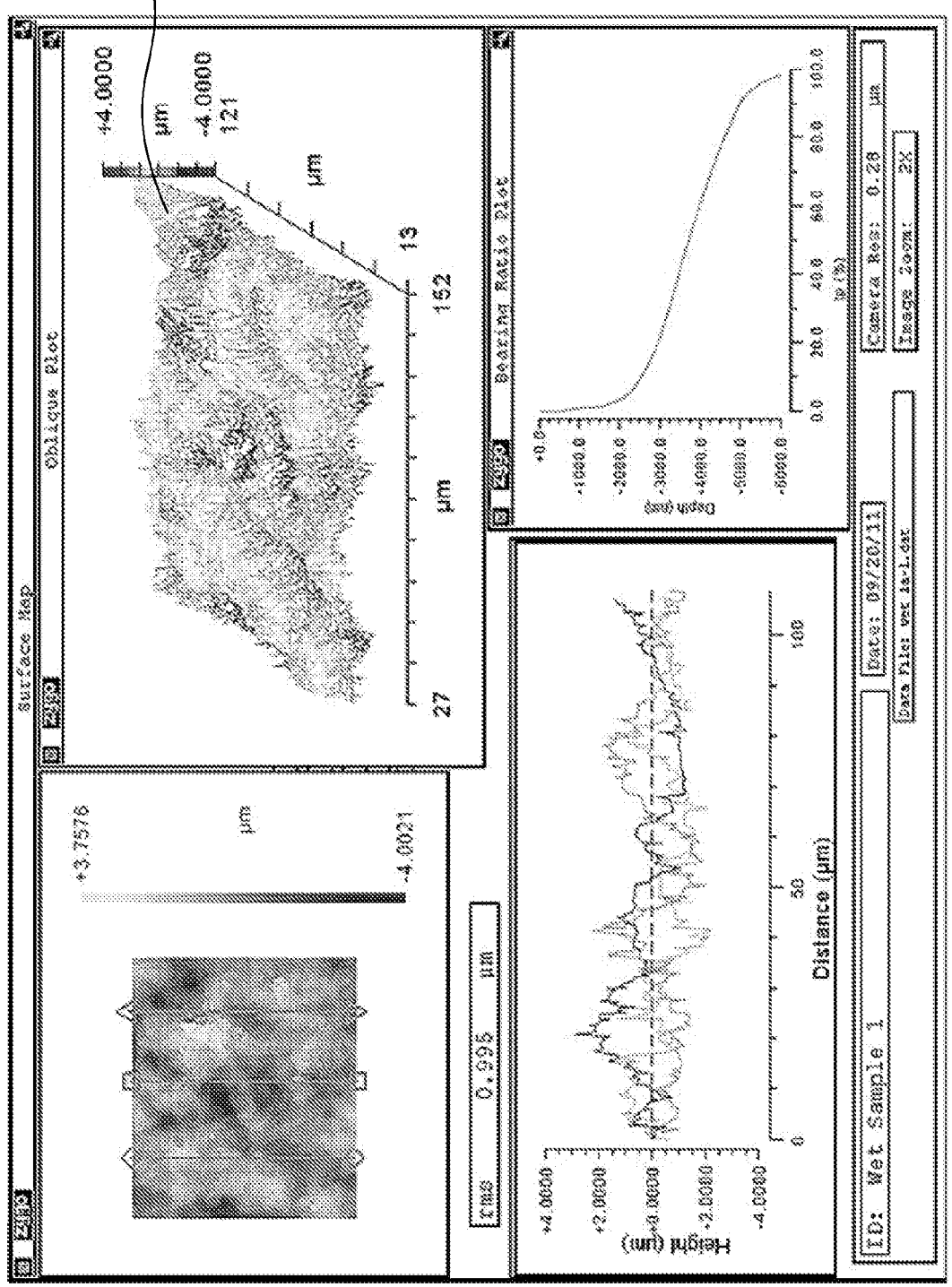
FIG. 20 depicts a surface scan at 40× magnification of wet sample 1.
Figure 21:
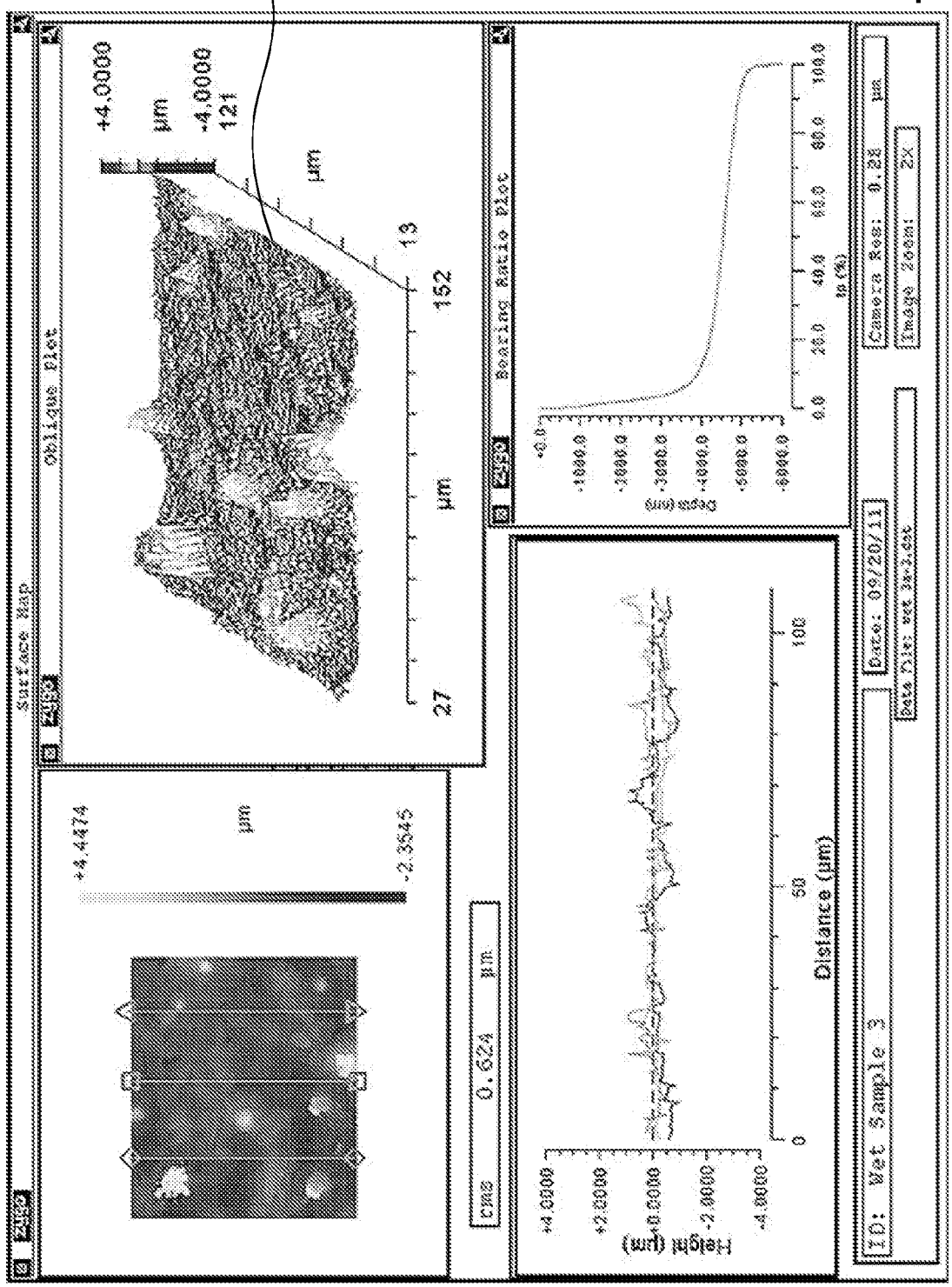
FIG. 21 depicts a surface scan at 40× magnification of wet sample 3.

FIGS. 16-18 depict surface scans at 5× magnification of dry sample 5, wet samples 1 and 3, respectively. FIGS. 19-21 depict surface scans at 40× magnification of dry sample 5, wet samples 1 and 3, respectively. The surface plot 74 of each figure represents the surface texture of a profile. Each plot 74 serves as a means for verifying that the scans of FIGS. 3A-9J qualitatively match the scans provided by SEM.

Figure 22:
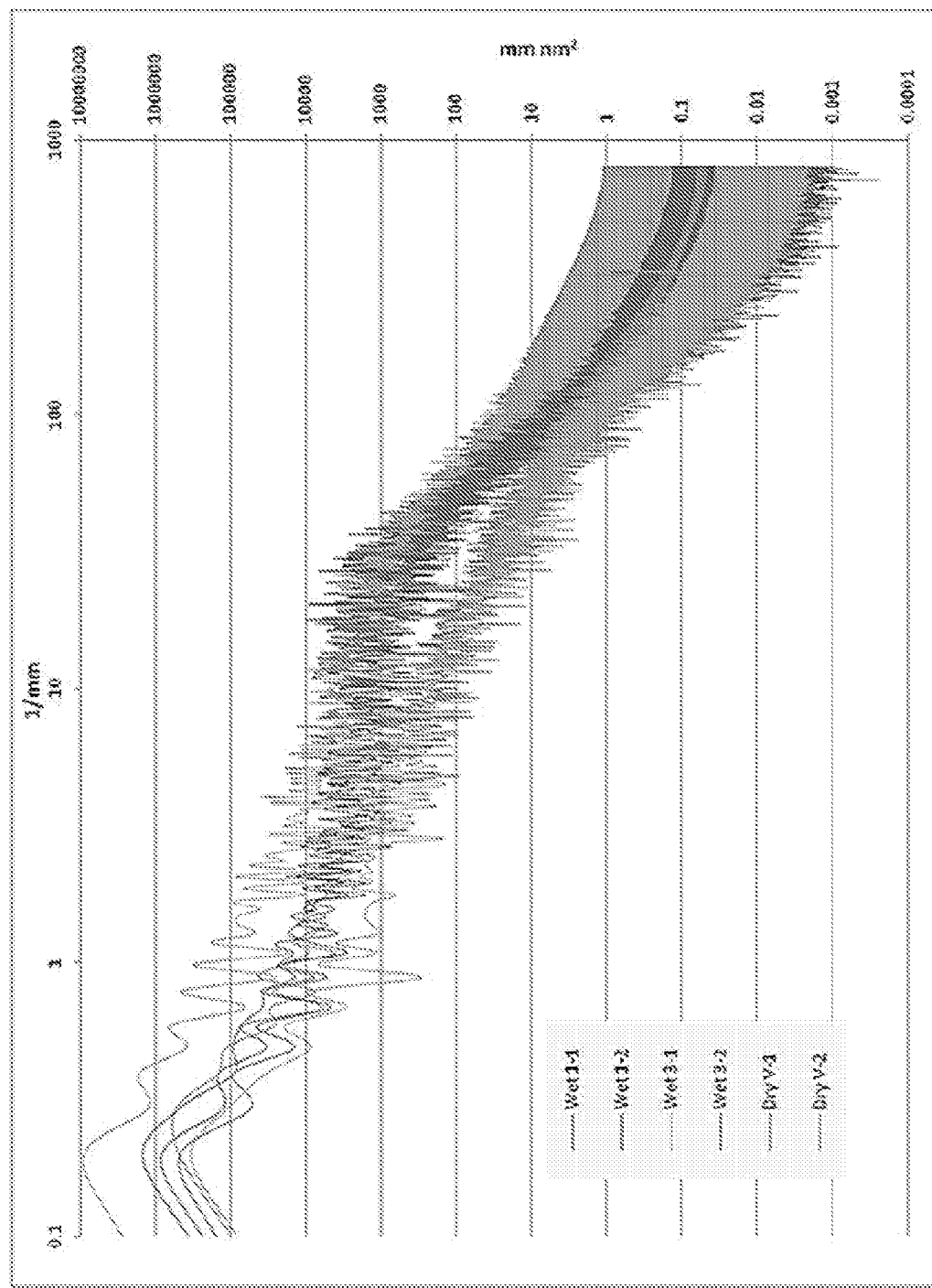
FIG. 22 depicts Power Spectral Density (PSD) of two samples each of dry sample 5, wet samples 1 and 3.
Figure 23:
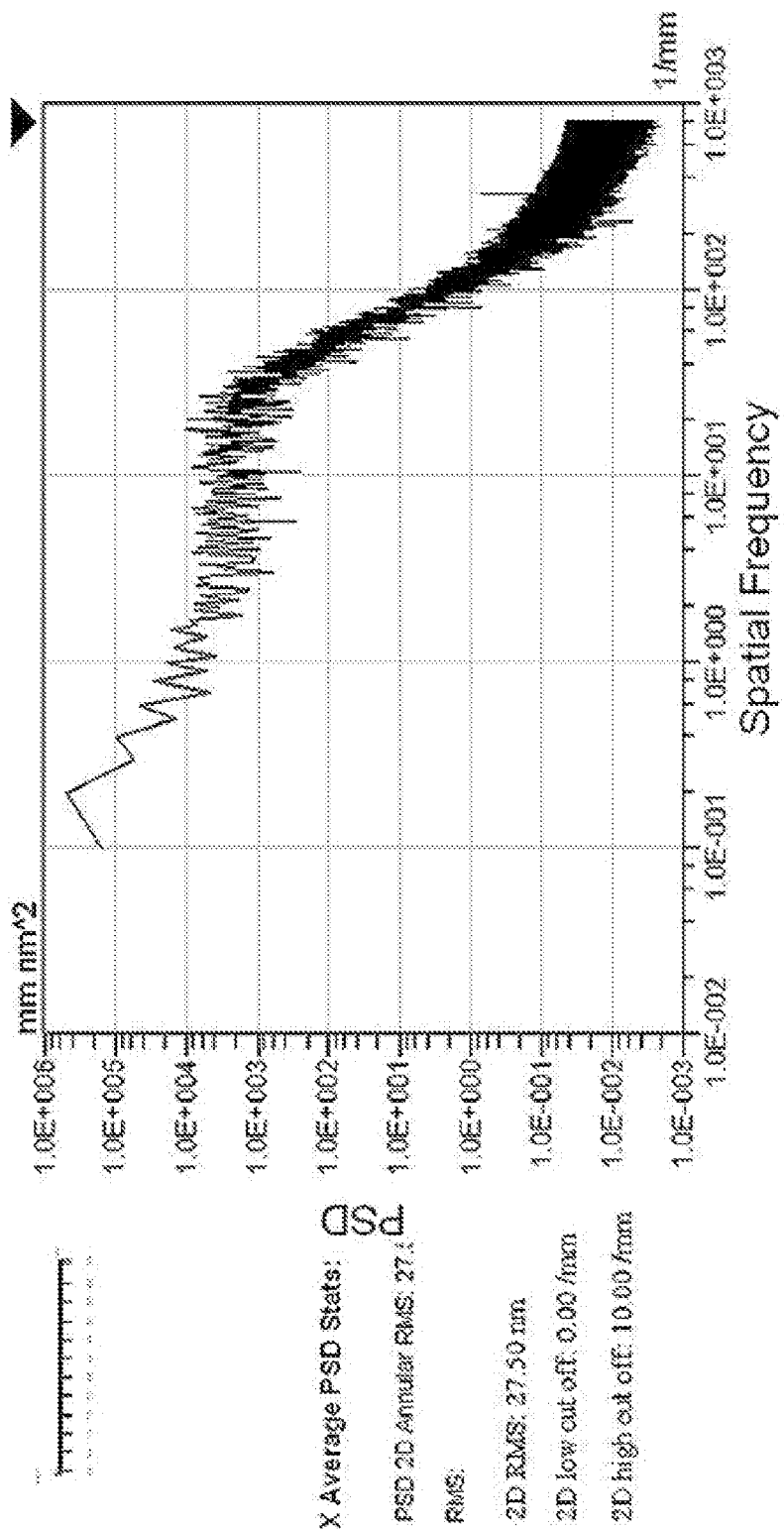
FIG. 23 depicts PSD of a first wet sample 1.
Figure 24:
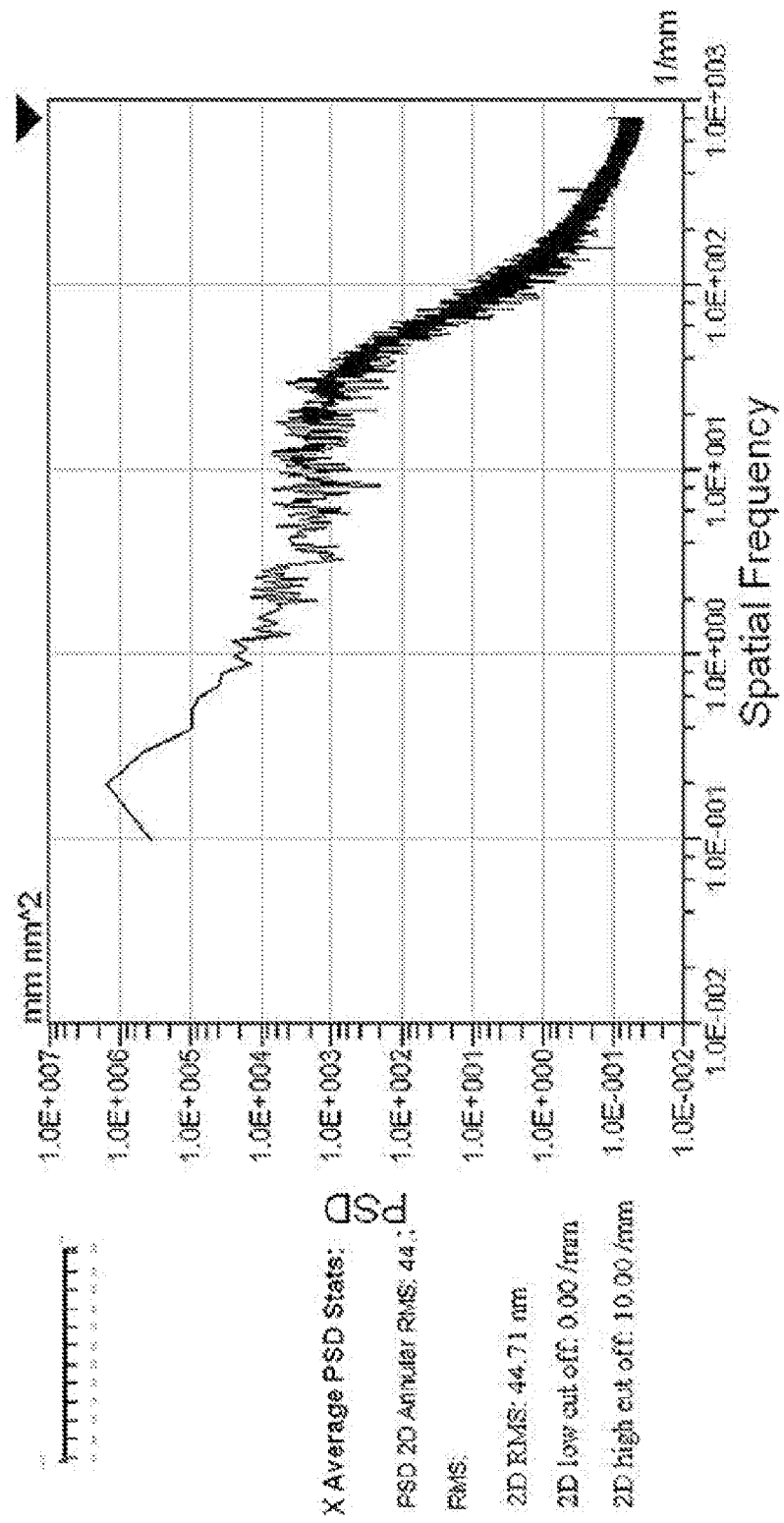
FIG. 24 depicts PSD of a second wet sample 1.
Figure 25:
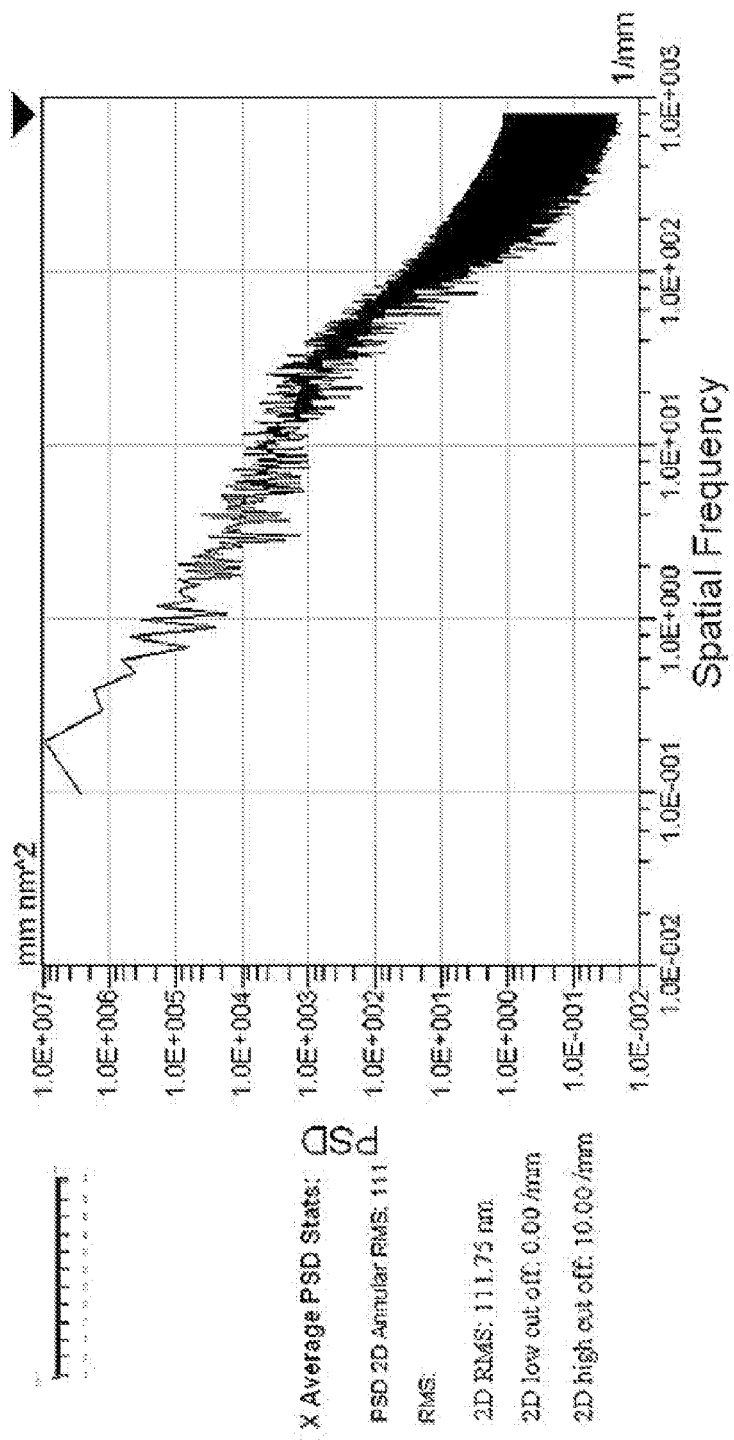
FIG. 25 depicts PSD of a first wet sample 3.
Figure 26:
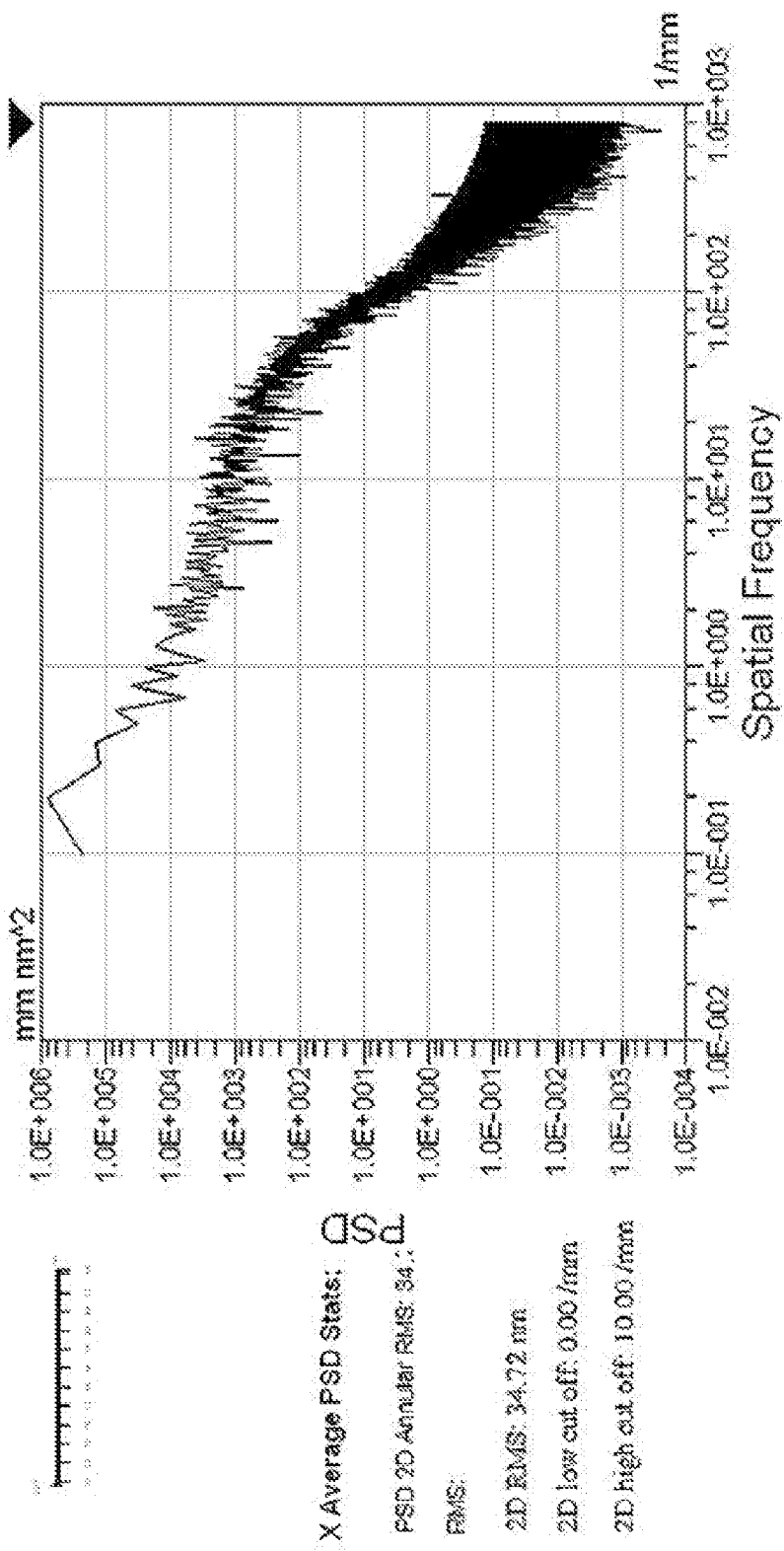
FIG. 26 depicts PSD of a second wet sample 3.
Figure 27:
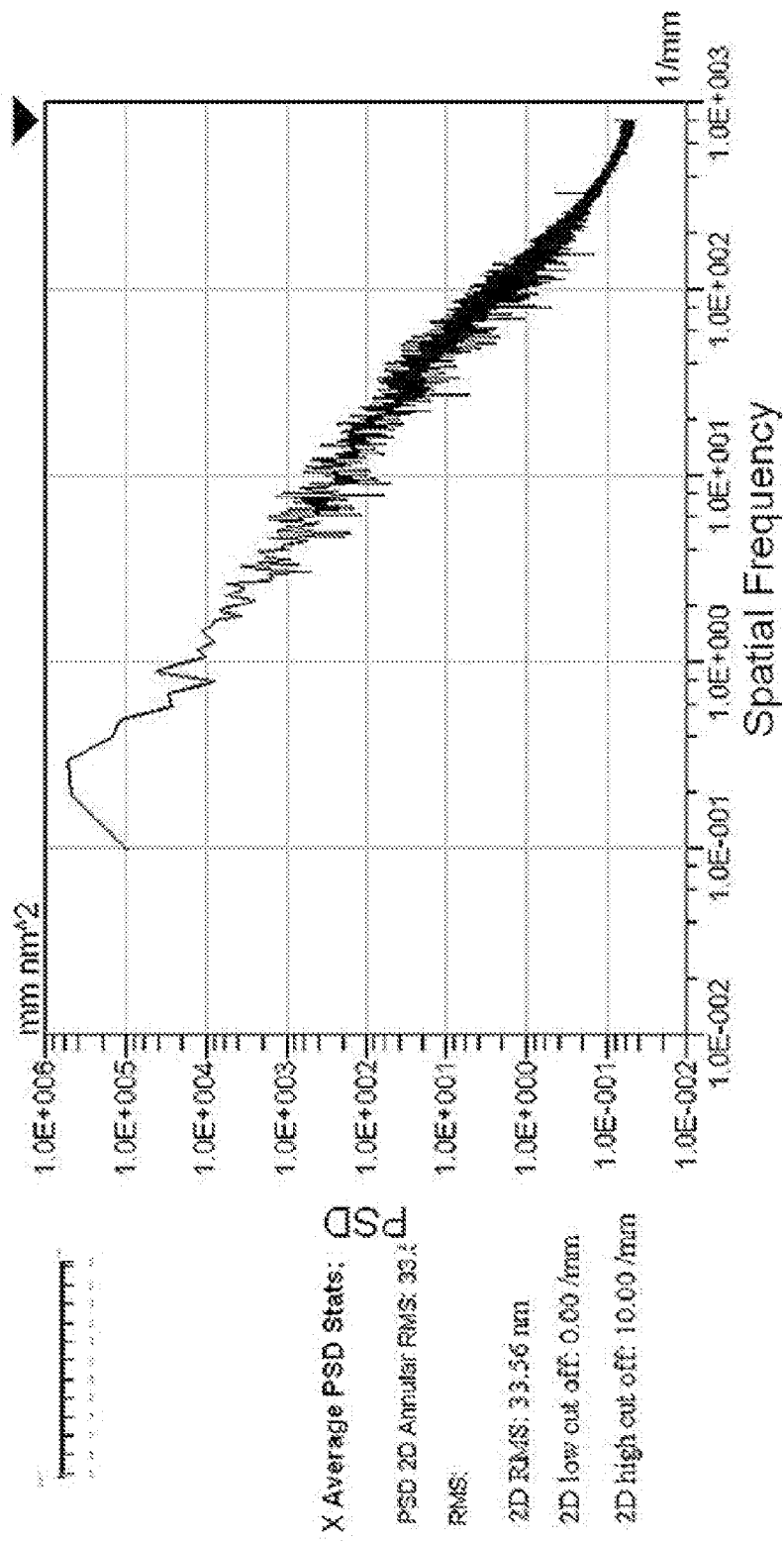
FIG. 27 depicts PSD of a first dry sample 5.
Figure 28:
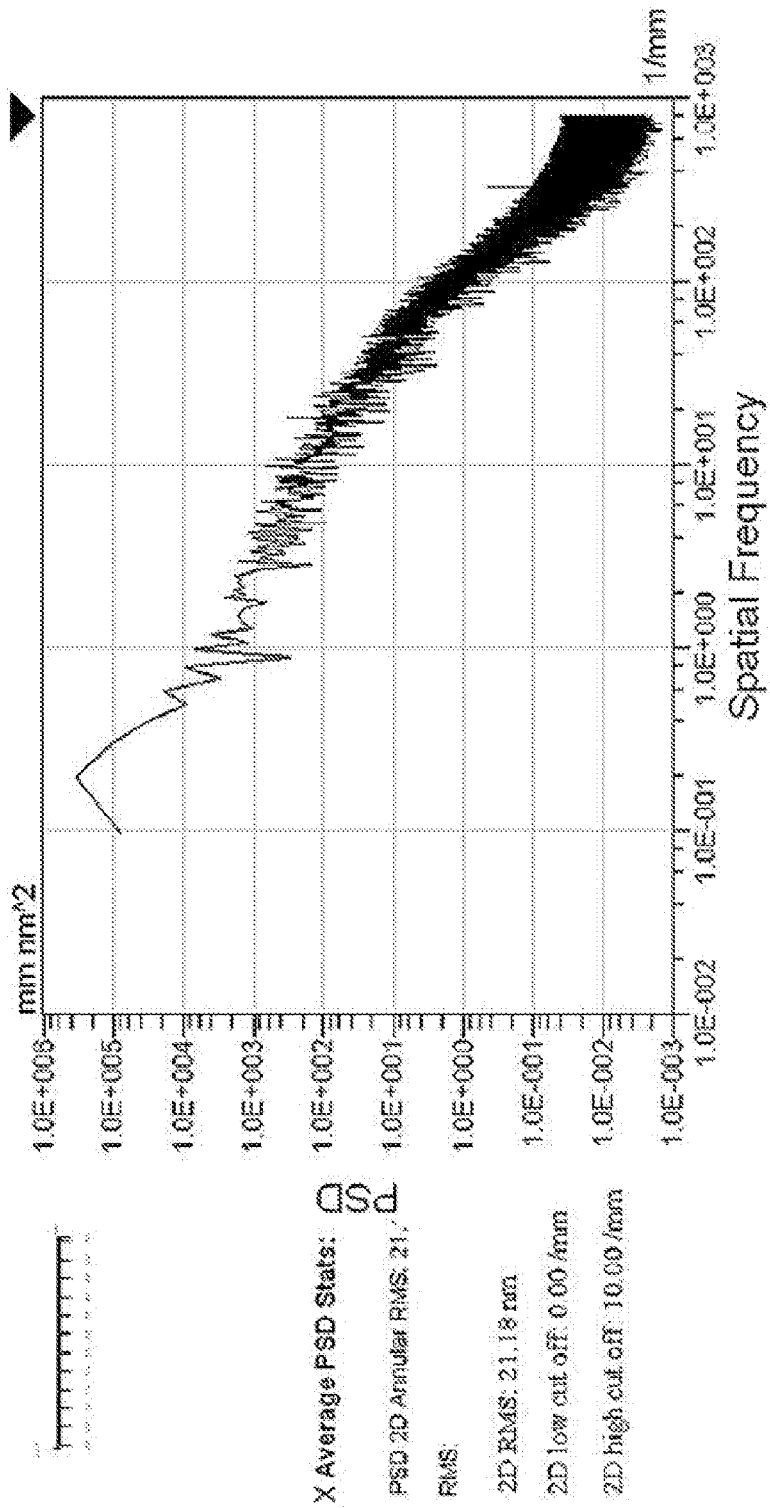
FIG. 28 depicts PSD of a second dry sample 5.

FIG. 22 depicts Power Spectral Density (PSD) of two samples each of dry sample 5, wet samples 1 and 3. The measurements were performed using a high resolution surface profiler. A total of two measurements were taken on each sample at a trace length of 5.6 mm. All profiles are depicted in FIG. 22 for comparison purposes.

FIG. 23-28 depict individual PSD traces of wet sample 1, wet sample 3 and dry sample 5. The surface analyses of FIGS. 10-28 were performed per "Surface measurement and analysis per ASME B46.1-2009 Surface Texture, Surface Roughness, Waviness and Lay." FIG. 22 demonstrates that although combined in one chart, the six profiles which have been charted individually in FIGS. 23-28 clearly show distinct differences between the profiles. Therefore, FIG. 22 reinforces the presence of varying surface profiles.

Figure 29:
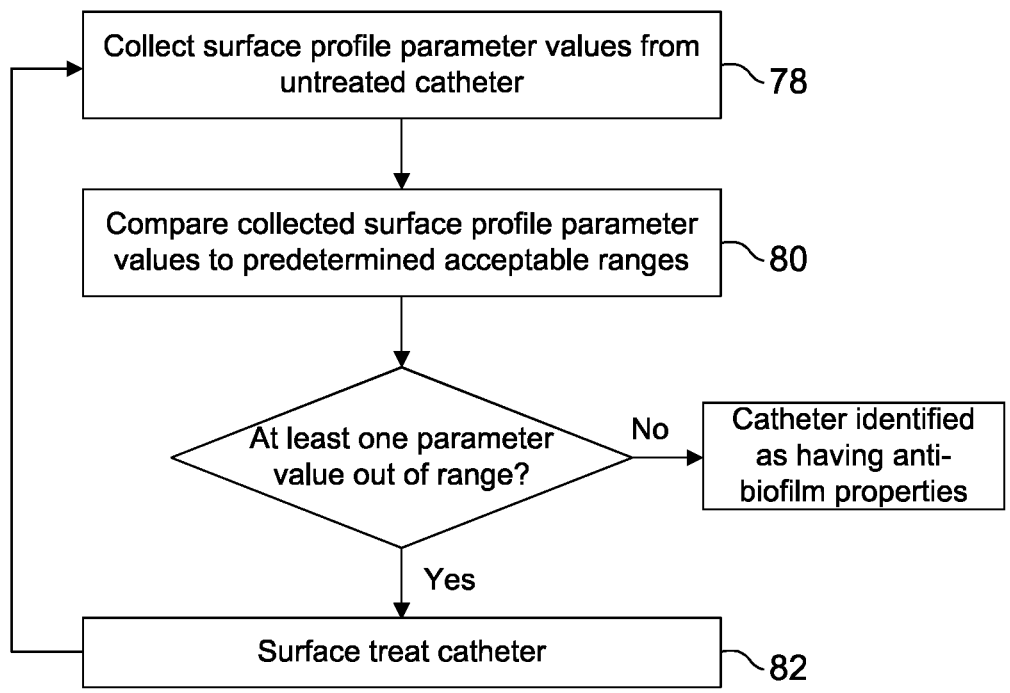
FIG. 29 depicts a series of steps for producing a suitable anti-biofilm catheter.

Applicant discovered that by following a series of steps, a suitable anti-biofilm catheter can be identified as depicted in FIG. 29. The surface of an untreated catheter is first collected using tools known in the art to determine key surface profile parameter values (step 78). Such parameters include, but not limited to kurtosis (Rku), skewness (Rsk), Rz, Rt, Ra, Rq, Rk and Rvk. In one embodiment, the untreated catheter is placed under a high resolution surface profiler. Such a profiler can be Zygo Corporation's NewView 500. The collected surface profile parameter values are then compared to their corresponding predetermined acceptable ranges of a surface suitable to be used as an anti-biofilm surface (step 80). Applicant identified acceptable ranges of surface profile parameter values as follows:

Rsk—from about −0.01 to about −0.6
Rku—from about 2.7 to about 3.3
Rz—about 4.0
Rt—about 5.7
Ra—from about 0.6 to about 0.8
Rq—from about 0.8 to about 1.0
Rk—from about 2.00 to about 2.55
Rvk—from about 0.95 to about 1.15

In one embodiment, if at least one surface profile parameter value falls outside of its predetermined acceptable range, then a surface treatment technique is applied to the catheter (step 82). In another embodiment, if at least one of the collected Rsk and Rku values falls outside of its predetermined acceptable range, then a surface treatment technique is applied to the catheter (also represented in step 82). Suitable surface treatment techniques include, but not limited to, coating (spray coating, dip coating or electrostatic coating) and polishing. Upon completing step 82, key surface profile parameter values are again obtained. If all of the newly collected catheter surface profile parameter values fall within their respective ranges, the catheter is determined to exhibit anti-biofilm properties and the catheter is ready for use. If at least one surface profile parameter value again falls outside of its predetermined acceptable range, then another surface treatment technique is employed and the aforementioned process is repeated.

I claim:

1. A anti-biofilm catheter comprising:
    a catheter adapted to be disposed within a patient's luminal system, wherein a portion of said catheter will come into contact with blood within said luminal system; and
    wherein said catheter portion includes a surface having a surface profile having a skewness value of from about −0.01 to about −0.6, a kurtosis value of from about 2.7 to 3.3, and an Ra value of from about 0.6 to about 0.8;
    whereby few components of said blood will attach themselves to said surface.

2. The anti-biofilm catheter of claim 1, wherein said profile further comprises an Rz value of about 4.0.

3. The anti-biofilm catheter of claim 1, wherein said profile further comprises an Rt value of about 5.7.

4. The anti-biofilm catheter of claim 1, wherein said profile further comprises an Rq value of from about 0.8 to about 1.0.

5. The anti-biofilm catheter of claim 1, wherein said profile further comprises an Rk value of from about 2.00 to about 2.55.

6. The anti-biofilm catheter of claim 1, wherein said profile further comprises an Rvk value of from about 0.95 to about 1.15.

7. The anti-biofilm catheter of claim 1, wherein said catheter is pre-formed to an in-use length.

8. The anti-biofilm catheter of claim 1, wherein said surface is attached to said tubing.

9. The anti-biofilm catheter of claim 1, wherein said surface is integrally formed with said tubing.

10. A method for producing an anti-biofilm catheter having at least one surface, said method comprising;
    (a) collecting surface profile parameter values of said at least one surface of said catheter, wherein said surface profile parameter values comprise Rsk and Rku values;
    (b) comparing Rsk and Rku values to corresponding predetermined acceptable ranges of a surface suitable to be used as an anti-biofilm surface, wherein said corresponding predetermined acceptable ranges comprise:
    (i) Rsk of from about −0.01 to about −0.6;
    (ii) Rku of from about 2.7 to about 3.3;
    (c) treating said at least one surface, if at least one of said Rsk and Rku values falls outside of said corresponding predetermined acceptable range and repeating steps (a) through (c) if at least one of said Rsk and Rku values falls outside of said corresponding predetermined acceptable range.

* * * * *